(12) United States Patent
Dogariu

(10) Patent No.: US 7,307,734 B2
(45) Date of Patent: Dec. 11, 2007

(54) INTERFEROMETRIC SENSOR FOR CHARACTERIZING MATERIALS

(75) Inventor: Aristide Dogariu, Winter Springs, FL (US)

(73) Assignee: University of Central Florida, Orlando, FL (US)

( * ) Notice: Subject to any disclaimer, the term of this patent is extended or adjusted under 35 U.S.C. 154(b) by 188 days.

(21) Appl. No.: 10/919,223

(22) Filed: Aug. 16, 2004

(65) Prior Publication Data

US 2005/0190372 A1 Sep. 1, 2005

Related U.S. Application Data

(60) Provisional application No. 60/494,967, filed on Aug. 14, 2003.

(51) Int. Cl.
*G01B 9/02* (2006.01)
(52) U.S. Cl. ....................................... 356/497
(58) Field of Classification Search ................ 356/479, 356/497, 335, 336
See application file for complete search history.

(56) References Cited

U.S. PATENT DOCUMENTS

| | | | |
|---|---|---|---|
| 3,958,560 A | 5/1976 | March | |
| 5,202,745 A | 4/1993 | Sorin et al. | |
| 5,323,229 A | 6/1994 | May et al. | |
| 5,365,335 A | 11/1994 | Sorin | |
| 5,433,197 A | 7/1995 | Stark | |
| 5,646,724 A | 7/1997 | Hershline | |
| 5,835,215 A | 11/1998 | Toida et al. | |
| 5,847,827 A | 12/1998 | Fercher | |
| 5,962,852 A * | 10/1999 | Knuettel et al. ........ 250/339.11 |
| 6,152,875 A | 11/2000 | Hakamata | |
| 6,256,103 B1 | 7/2001 | Sorin et al. | |
| 6,525,823 B1 | 2/2003 | Dogariu et al. | |
| 6,738,144 B1 * | 5/2004 | Dogariu ...................... 356/479 |

OTHER PUBLICATIONS

Bruulsema et al., Correlation between blood glucose concentration in diabetics and noninvasively measured tissue optical scattering coefficient, 1997, Optics Letters 22(3):190-192.
Popescu et al., Optical path-length spectroscopy of wave propagation in random media, 1999, Optics Letters 24(7):442-444.

* cited by examiner

Primary Examiner—Hwa (Andrew) Lee
(74) Attorney, Agent, or Firm—Pepper Hamilton LLP

(57) ABSTRACT

An integrated optical sensor, using low coherence interferometry, is capable of determining analyte concentration in a material sample based on absorption, scattering and polarization. The sensor includes one or more light collectors, with each collector having a separation distance from the region where the sample is illuminated by the source. The light backscattered from the sample is combined with reference arm light at the same optical path length for each light collector. The intensity of interference may be correlated with the concentration of an analyte in the material, for example the glucose concentration in a turbid medium like skin. The sensor operation can be based on fiber optics technology, integrated optics, or a combination of these. The operation is such that the spectrally resolved scattering and absorption coefficients can be measured simultaneously. In addition, the operation of the sensor can be synchronized with other sensors, for example temperature, pressure, or heartrate.

43 Claims, 19 Drawing Sheets

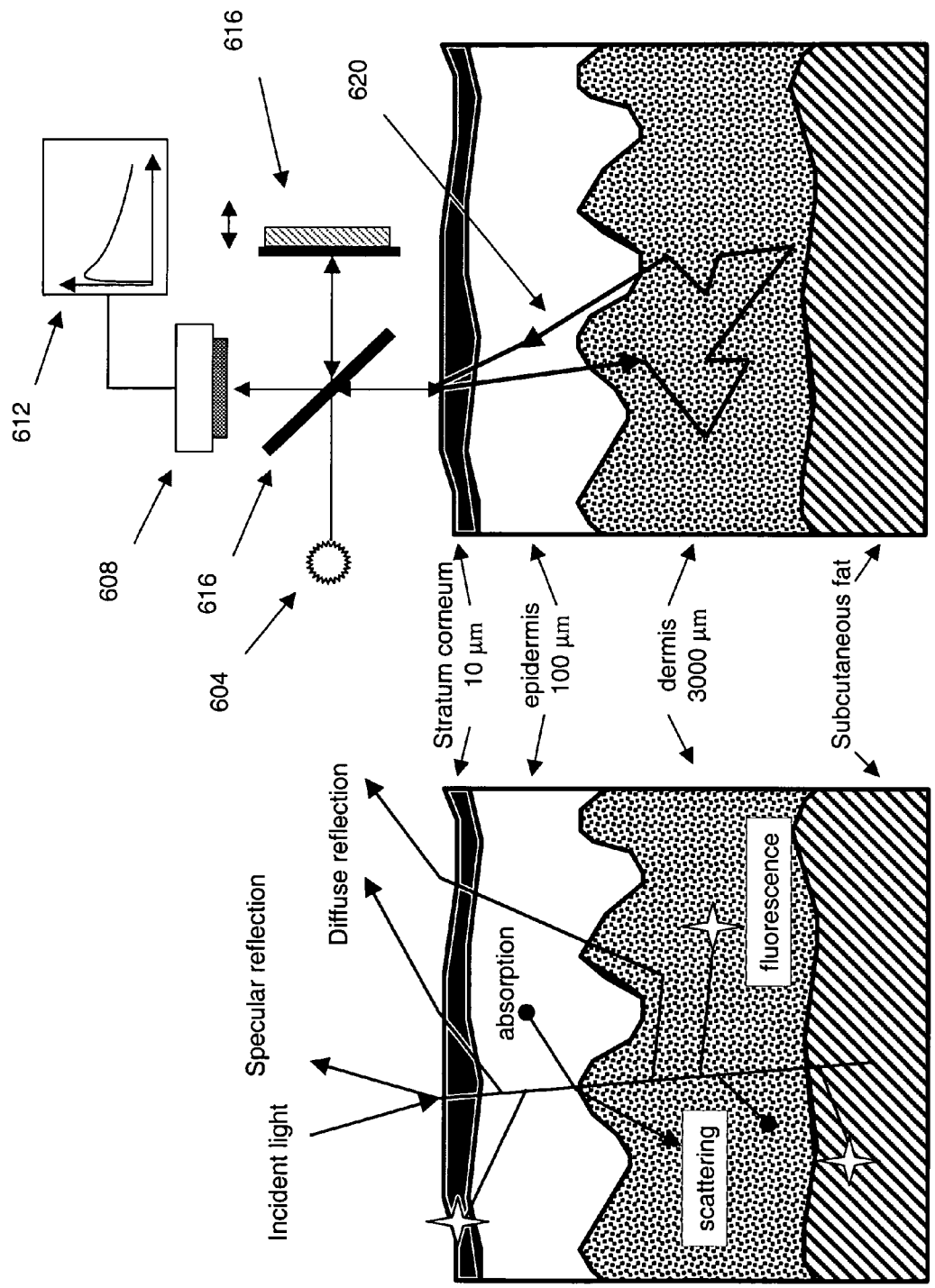

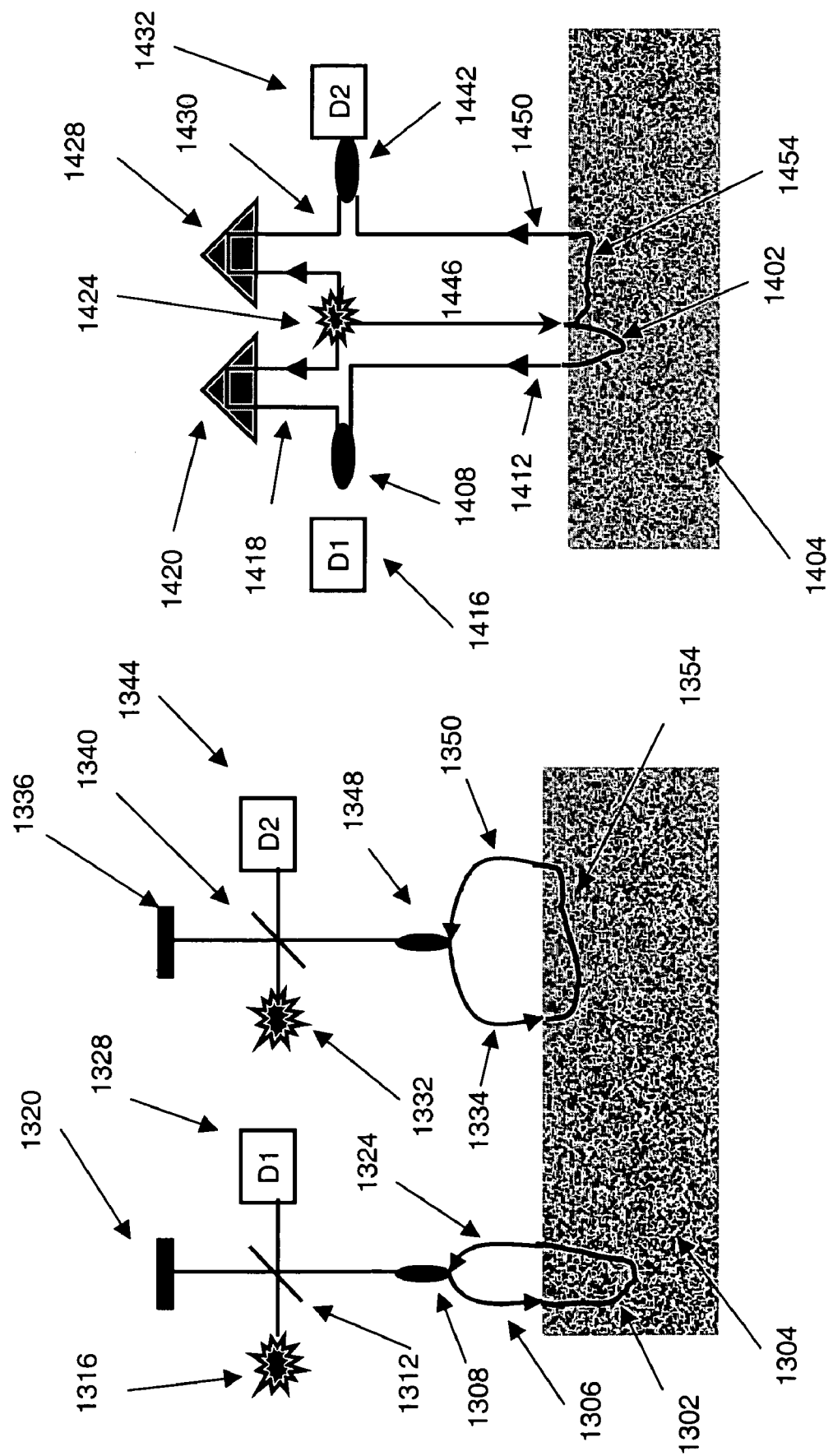

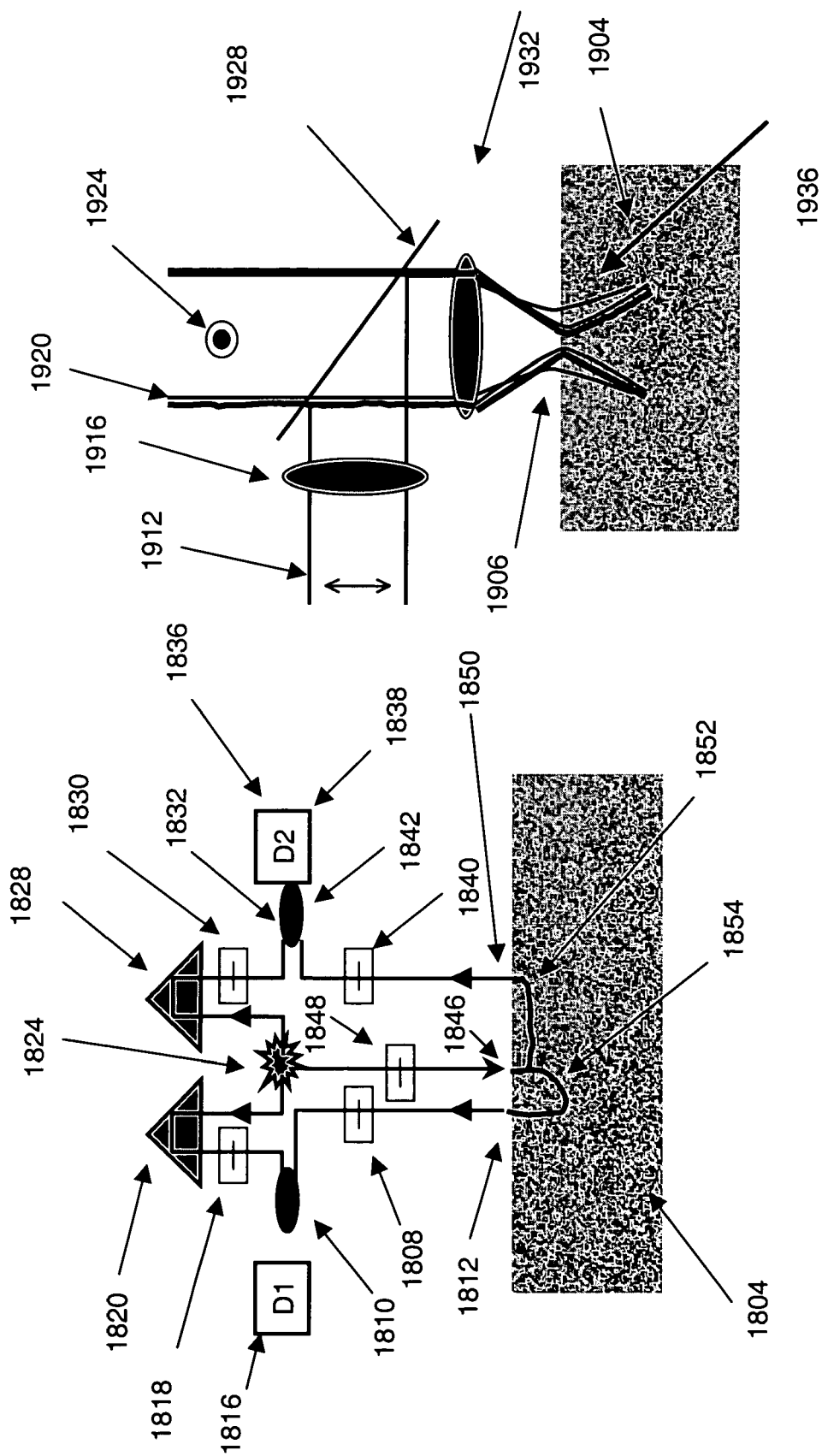

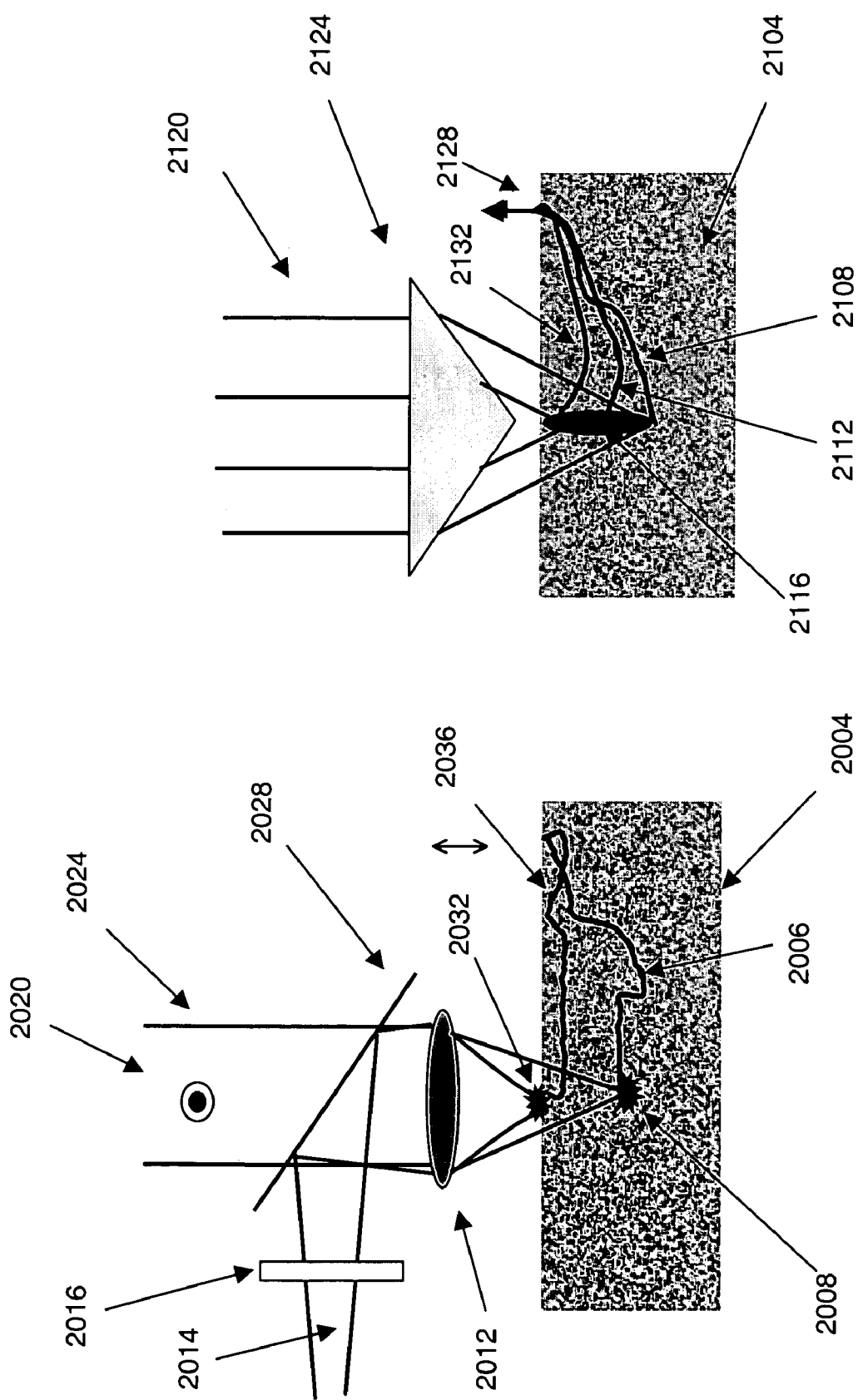

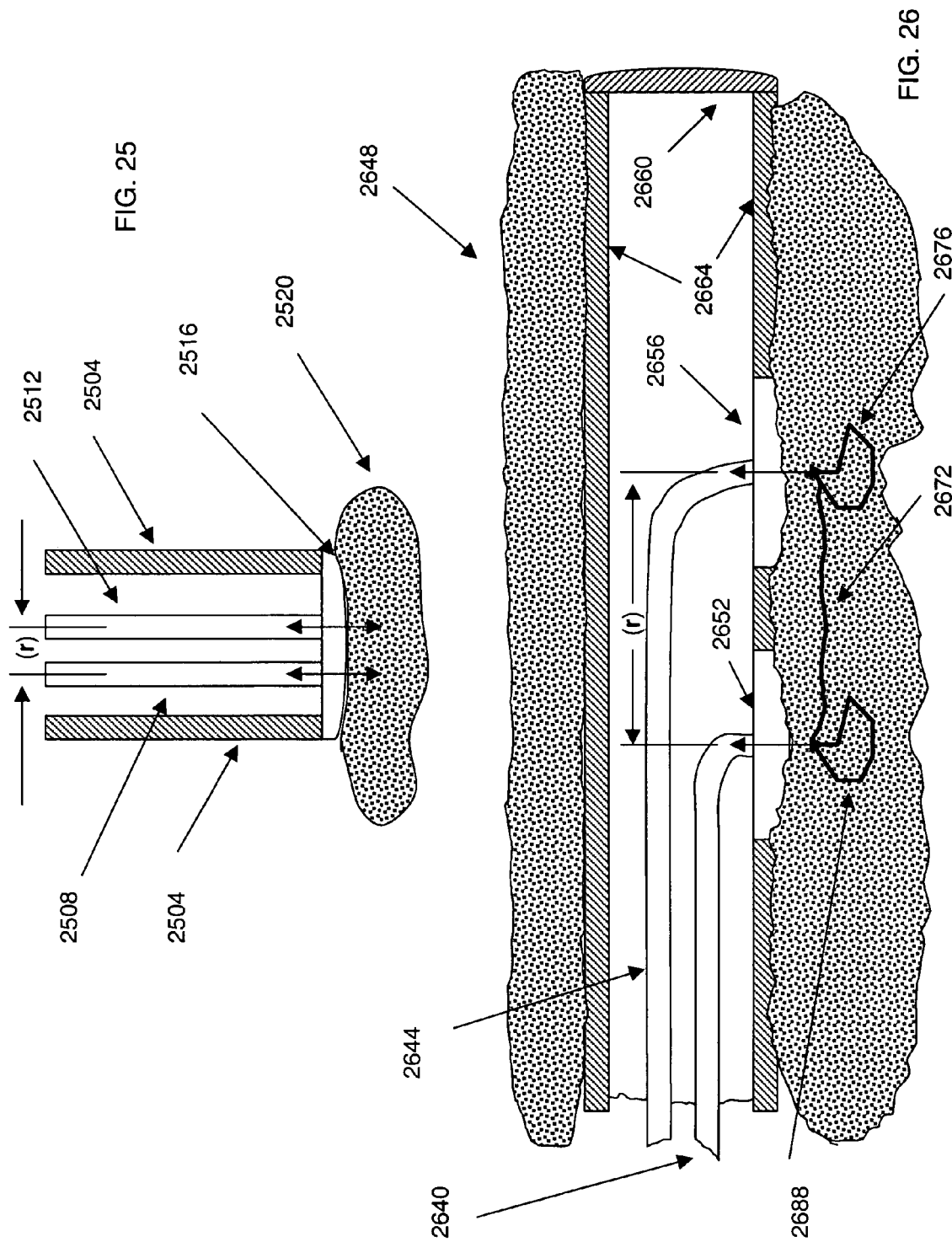

INTERFEROMETRIC SENSOR FOR CHARACTERIZING MATERIALS

CROSS REFERENCE TO RELATED APPLICATIONS

This application claims the benefit and priority of U.S. Provisional Application Ser. No. 60/494,967 filed Aug. 14, 2003 the contents of which are incorporated herein by reference in their entirety.

BACKGROUND

When a light scattering material, for example a biological tissue or a polymer film containing dispersed colloidal particles, is examined using methods like infrared absorption spectroscopy, information about the material including the concentration of an analyte in the material (solvent, glucose, drug) may be lost due to light scattering by the material. Non-invasive monitoring of patient during a course of treatment, for example monitoring a patient undergoing chemotherapy, monitoring the uptake of topically applied drugs in a patient, or monitoring glucose concentration in a diabetic patient offers many advantages over invasive measurements since non-invasive monitoring could be performed intermittently or continuously by the patient and without the need to withdraw of blood or perform complex chemical tests. Intermittent blood glucose tests, which are widely practiced by diabetic patients, involve pain and discomfort from frequent finger pricking.

There are several electro-chemical methods to determine blood glucose concentration, which require collecting a small blood sample. There are optical approaches for monitoring glucose concentration in patients that do not require collecting biological samples. These optical techniques have primarily focused on measuring glucose concentration by following the changes in the optical properties in the aqueous chamber located between the crystalline lens and cornea. The reason for this is that the biological fluid examined is relatively homogeneous and scattering is rather weak. Examples are: U.S. Pat. No. 3,958,560 that discusses near infra-red (NIR) optical activity in the aqueous humor: U.S. Pat. No. 5,835,215 that discloses absorbance in the aqueous humor; U.S. Pat. Nos. 5,433,197 and 6,152,875 wherein the refractive index of the aqueous humor are discussed.

Blood plasma comprises around 20% of the body's extracellular fluid and is very similar in composition to interstitial fluid except that interstitial fluid primarily contains much less protein, around 2% by volume compared to blood plasma because most of the plasma protein molecules are too large to pass through the capillary walls into the interstitial area. The small amount of protein which does pass through the capillary walls is eventually taken up by the lymph and then ultimately returned to the blood. The relative proportions of plasma proteins can vary in certain diseases and can be a useful diagnostic aid. For example, albumin is among the smallest of the plasma proteins is just small enough to pass through capillary walls. In a healthy patient, this leads to a small amount of albumin in the interstitial fluid. However in patients with kidney disease large amounts of albumin may to leak out through the damaged kidney tubules and may be detected in the interstitial fluid or urine. Blood has a complex composition, and some of the various components include those shown in Table 1.

TABLE 1

| Blood Components | Reference Range |
| --- | --- |
| Water | 78-78.8 g/dl |
| Hemoglobin | 6-18 g/dl |
| Glucose | 40-500 mg/d |
| Cholesterol | 80-800 mg/dl |
| Albumin | 3-5 g/dl |

Analysis of various plasma components may be made using spectroscopic measurements. The mid- and near-IR spectral ranges are of special importance for spectroscopic identification and analysis using absorption spectroscopy. The mid-IR ($\lambda$=2.5µ to 25µ; $\omega$=4000–400 cm$^{-1}$) is useful for molecular identification; each absorption band in the spectrum of a molecule corresponds to a vibrational transition within the molecule and gives a measure of the frequency at which the vibration occurs.

In materials that have one or more components with different refractive indices, it may be difficult to obtain information about a material or an analyte concentration in the material directly from an absorption spectrum because of light scattering. There is a need to isolate the influence of scattering from absorption coefficients in a variety of materials like human skin which is a highly heterogeneous, multi-layer medium whose optical properties are rather specific to each individual. For other turbid and optically dense materials that exhibit multiple light scattering, such as a polymer having dispersed colloidal particles or a bacterial slime film growing on a surface, the absorption characteristics of these materials and interstitial molecules in the materials can also be obscured by scattering of incident light from the spectrometer. It would be advantageous to characterize optically dense materials using an apparatus and method that can independently determine the scattering and absorption coefficients of the material from light incident on the material.

SUMMARY OF THE INVENTION

Embodiments of the present invention relate to an apparatus and method for using the apparatus to independently determine the absorption and scattering coefficients from light backscattered from an illuminated sample. The apparatus is an interferometer that can independently adjust the distance between one or more detection sample points (r) and adjust the path length (s) of the interferometer so that the backscattered light measured at the one or more sample points each have the same optical path length (s). The apparatus, which may be configured as a sensor, utilizes path length resolved backscattering intensity from one or more light collector sample points positioned about the sample to determine the absorption and scattering coefficients of the sample.

The apparatus may be a sensor that can be used to characterize various optically dense or diffuse materials and detect interstitial molecules present in the materials. The materials can include but are not limited to polymers, polymer composites, organs and tissues including skin. Interstitial molecules may include but are not limited to solvents, components of blood plasma, or drugs given to a patient. Preferably the sensor is used to correlate the concentration of molecules present in the interstitial fluid of tissues with the absorption measured by the sensor. Molecules present in the blood plasma and intracellular fluids can be found in the interstitial fluid and can be detected by the sensor of the present invention and may be used to characterize the course of treatment of a patient, the state of a disease, or the transport of a drug. Various tissues including but not limited to skin, arteries, muscle, and the colon may be characterized by the sensor of the present invention.

One embodiment of the present invention is an interferometer based optical sensor that includes a low coherence light source and a light splitter or coupler positioned to direct a portion of the light from the source to a material or tissue sample and a portion of the light to a reference arm. The light from the source interacts with the sample and can be absorbed, reflected, backscattered, or a combination of these by the sample. The other portion of the source light from the light splitter is directed to the interferometer reference arm, the reference arm capable of being adjusted to a select or desired physical path length, optical path length, or optical delay.

In the optical sensor, a sample light collector is positioned to collect a first backscattered light from the light source interacting with the sample. The first sample light collector is coupled with a detector that generates a first signal in response to interference between the first backscattered light and light from the reference arm at the optical path length which can be coupled together by a first light combiner such as a fiber coupler, a lightsplitter cube or light splitter plate. A second sample light collector, with the second sample light collector positioned apart from the first sample light collector on the sample, collects backscattered light from the light source interacting with the sample. The light from the second sample light collector and light from the reference arm set to the optical path length are coupled together by a second light combiner and interference between the backscattered light and light from said reference arm is measured by a second detector. In a preferred embodiment of the optical sensor, the light source and first light collector are a transceiver. In a more preferred embodiment the light source and the second light collector are also a transceiver.

A processor can be configured to take a signal from the detector related to interference between the first light collector and reference arm light and a signal from the detector related to interference between the second light collector and reference arm light and use the signals to calculate a quantity or value proportional to the absorbance of the sample, calculate a quantity or value proportional to the scattering of the sample, calculate both the absorption and scattering of the sample. The scattering and absorbance calculated may be related through a correlation function to the concentration of a target analyte in the sample. Alternatively the scattering and absorbance calculated may be related through a correlation function to the type of material present in the sample. Examples of target analytes in polymeric materials may include but are not limited to solvents, plasticizer, and unreacted monomers. Examples of target analytes in biological tissues may include glucose, albumin, drug molecules, or various proteins. Examples of different types of materials or tissue include the detection of different types of arterial placque in arteries or the growth of bacterial slime on conduit surfaces.

The optical sensor in embodiments of the present invention may be used to non-invasively monitor glucose concentration in a tissue like skin to determine the status of patients having diabetes. In tests where protein molecules are injected intradermally into the skin of a patient and the change in protein absorption used to monitor the lymphatic function of the skin, the optical sensor in embodiments of the present invention may be used to non-invasively characterize the protein absorption and provide a measure of the health of the patient.

The interferometric sensor may include a housing to enclose elements of the sensor and protect them from direct contact with the sample. The housing may include a low coherent light source and the first and second light collectors or optionally one or more transceivers can be positioned within the housing. Preferably the first and second sample light collectors are positioned within the housing so that they are capable of collecting light backscattered from the sample from one or more points on the sample away from the point where light is injected into the sample. In one version of the present invention the sensor is configured to be placed on the surface of a sample material such as a piece of body tissue, an agricultural produce item, or a man-made article like a composite polymer or coating. The sensor can used to measure independently the absorption and diffusion coefficients (inversely proportional to the scattering coefficient)s of the sample which may be correlated to the concentration of molecules like glucose, unreacted monomers, or proteins in the material. Alternatively the sensor may be inserted into a sample, such as but not limited to an artery, the esophagus, a wound, or other body cavity. The sensor housing couples light from the low coherent source into the sample and contacts one or more light collectors in the housing with the wall or surface of the tissue whereby the absorption and diffusion coefficients of the sample are independently determined and related to a condition, a type of tissue, a disease state in a tissue, or progress in a course of treatment. The sensor and housing of the present invention may be incorporated into a laparoscope or endoscope.

To provide for different spacings between the light collectors (r), the sensor or housing may also include a mechanism that can be used to change the position of the first and second light collectors relative to each other. Alternatively, a fiber optic switch can be used to sample a plurality of fixed optical fibers or channel waveguide sample light collectors, with each fiber optic sample light collector or channel waveguide having a different separation distance from the source light interacting with the sample. Preferably the position of one of the light collectors with respect to the source light is such that the light collector samples light having a trajectory dominated by sample absorption.

Another embodiment of the present invention is a method of characterizing a sample with an interferometer that includes setting a reference arm of the interferometer to an optical path length or optical delay and emitting low coherent light from a source into a light splitter. The light splitter directs a portion of the light to a region of the sample to generate backscattered light and the light splitter or coupler directs a portion of the source light to the reference arm of the interferometer which can be set to a predetermined optical path length. The region where light is directed or injected into the sample can be altered depending upon the size of the optical fiber, beam diameter, size of the waveguide, or lens used to propagate the source light to the sample.

Backscattered light from the sample may be collected from the region where light is directed and from one or more points on the sample away from the region on which the low coherent source light is directed. Backscattered light from the one or more points of the sample can be coupled with light from the reference arm at the optical path length or delay and used to determine a path length resolved backscattering intensity that results from interference at the optical path length between the reference arm light and the light backscattered from the one or more points on the sample. Signals from a detector proportional to the path length resolved backscattering intensities may be used as input for a processor for calculating an absorbance, calculating the scattering, or calculating the absorbance and scattering coefficients of the sample.

Another embodiment of the present invention is an interferometer based optical sensor for glucose monitoring in biological sample or tissue like skin, that includes a low coherence light source that can be directed or injected into a sample, one or more reference arms which may be adjusted to control the optical path length or optical delay of the reference arms, one or more sample light collectors to receive backscattered light from different points on the sample, detectors for measuring the interference between the reference arms and sample light collected, and a processor for calculating scattering and absorption coefficients of the sample based on recording spectral measurements over a limited range and determining glucose concentrations based on the spectral measurements.

Another embodiment of the present invention is a method for determining the identity of a material or the concentration of an analyte in a material or a tissue. Examples of analytes in materials may include low vapor pressure solvents or unreacted monomers. Examples of analytes in tissues may include sugar molecules such as glucose, drug molecules, or toxic materials absorbed through the skin. The concentration of an analytes like glucose may be determine in a sample or biological tissue using an interferometer based sensor that includes the acts of generating a low coherence light and directing into a sample, controlling the length of the optical path or the optical delay of the reference arm, measuring the backscattered light from the sample at one or more different points, the light collected at each point on the sample having the same optical path length or optical delay as the reference arm, independently calculating light scattering and absorption coefficients based on the interference between the collected light and reference arm light, and correlating the analyte concentration in the material or identifying the material from the absorption and scattering coefficients.

The optical sensor in embodiments of the present invention may be based on low coherence interferometry and may consist of elements from a free space device, fiber optic elements, integrated optics, or a combination of these. The sensor of the present invention provides an optical sensor that can that discriminate between light scattering and absorption and can be used to determine in real-time, the absorption and scattering of materials. The sensor is capable of determining the absorption of a material based on absorption, scattering, and polarization. The operation of the sensor utilizes path length resolved backscattering intensities, e.g. light having the same optical path length or optical delay, but having different trajectories within the sample which may be used to determine the contributions to the attenuation of the intensity of the source light on the sample due to scattering and absorption. The sensor may be used to characterize biological tissues by differences in their absorption, alternatively the sensor device and system can be used for the non-invasive monitoring of glucose concentration by characterizing the absorption of biological tissues, and preferably interstitial fluid in tissues. The optical sensor can be an integrated device and preferably has a long optical path with an acceptable signal to noise ratio (SNR). Utilizing these components, an integrated optical sensor that can determine the absorption and scattering characteristics of a sample can be made that is fast and inexpensive.

Advantageously, embodiments of the present invention permit the measurement of backscattered light using light collectors having a different separation distance (r) from the light source incident on the sample without the need for moving any light collectors. This can provide a more robust design by eliminating the need for positioners and calibration of light collector sensor positioning elements which can lead to improved accuracy.

Advantageously, embodiments of the present invention permit probing of different depths within the sample by adjusting the optical path length. This contrasts with a method and apparatus where the distance between the light collection site and a light introduction site corresponds to the depth from the surface into the sample at which scattering and absorption events that affect the intensity of the scattered light occur. Embodiments of the present invention permits external control of sampling depth facilitating use of the present device in laparoscopic and endoscopic housings where small size is important and differences in tissue and their composition can occur with small movements in position of the scope.

Advantageously, the optical sensor and method in embodiments of the present invention can be used to characterize a variety of materials. The sensor may be used as a non-invasive, fast, inexpensive, instrument for measuring the concentration of glucose in a skin, it may be used to characterize tissues such as arteries and other organs during endoscopic procedures, it may also be used to characterize complex composite materials in a variety of coating and material science applications.

Further objects and advantages of this invention will be apparent from the following detailed description and the accompanying drawings.

BRIEF DESCRIPTION OF THE FIGURES

FIG. 5 illustrates the layered structure of skin and the attenuation of incident light on the skin by various phenomena such as absorption and scattering.

FIG. 6 shows typical photon path length distributions for media with different optical densities such as human skin.

FIG. 13 shows a compact fiber optic-based device which includes two independent interferometers, each having the same optical path length, with different separation distances between the injection and collection points; the device illustrates a fiber optic based device with fixed delay lines.

FIG. 14 shows a fiber optic-based device that may be used to characterize a material that includes two interferometers with different separation distances between the injection and collection points. The interferometers share the same light source and each have their own reference path.

FIG. 18 shows a fiber optic-based device that includes one interferometer with polarization control elements that are fiber integrated. A similar structure can be based on an integrated design as illustrated in FIG. 15.

FIG. 19 shows an optical design for an optical head that permits two interferometers to share the same optical axis. The separation can be done by overlapping two lights with different polarizations. The two independent interferometers permit the illumination of two different volumes of the tested tissue sample.

FIG. 20 shows an optical design for the optical head that permits two interferometers to share the same optical axis. The separation can be done by overlapping two lights with different polarizations. The two independent interferometers permit the tissue to be sampled at different depths while maintaining the same path length.

FIG. 21 shows an alternate design providing a 'line' source within the tested material sample or tissue. The axicon geometry permits the generation of a long region of illumination within the sample material or tissue.

FIG. 25 illustrates an embodiment of a sensor housing for a device of the present invention with optical fibers transceivers separated by a distance (r) and positioned at the distal end of the housing that may be used to determine the absorption and scattering coefficient of a material or a tissue.

FIG. 26 illustrates an embodiment of a sensor housing for a device of the present invention with optical fibers positioned along the sidewall of a housing and separated by a distance (r) that may be used to determine the absorption and scattering coefficient of a material or a tissue.

DETAILED DESCRIPTION OF INVENTION

Before the present compositions and methods are described, it is to be understood that this invention is not limited to the particular structures, molecules, compositions, methodologies or protocols described, as these may vary. The invention is not limited in its application to the details of the particular arrangement shown since the invention is capable of other embodiments. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "photon" is a reference to one or more photons and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. "Optional" or "optionally" means that the subsequently described event or circumstance may or may not occur, and that the description includes instances where the event occurs and instances where it does not. All publications mentioned herein are incorporated by reference. Nothing herein is to be construed as an admission that the invention is not entitled to antedate such disclosure by virtue of prior invention.

Embodiments of the present invention relate to a device that measures the intensity of backscattered light from one or more points on a sample, the back scattered light detected at the points having the same optical pathlength or optical delay, but one or more different trajectories through the sample. The backscattered light from the different trajectories, but with the same optical path or optical delay are sampled by one or more light collectors and coupled with light from a reference arm. Preferably the trajectories of the low coherent light in the material include a trajectory having both scattering and absorption components as well as a trajectory having primarily an absorptive component. These different trajectories can be used to determine separately the contribution of absorption and scattering to the backscattered light intensity from the material.

Figure 1:
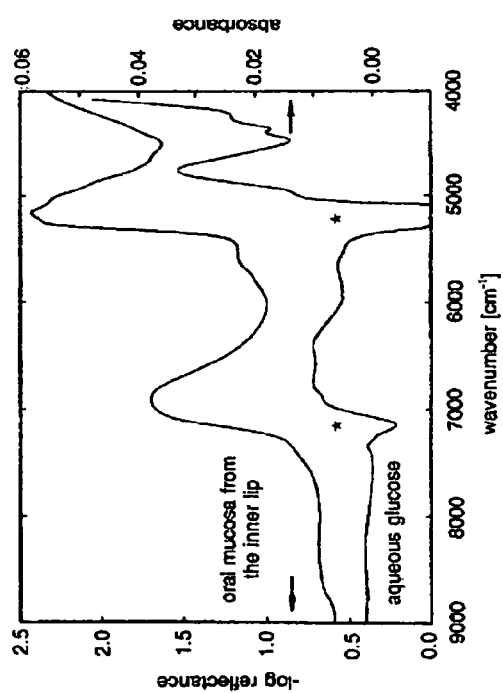
FIG. 1 is a prior art reflectance and absorption spectra of glucose from the inner lip of a subject and the absorption spectrum of an aqueous glucose solution.
Figure 2:
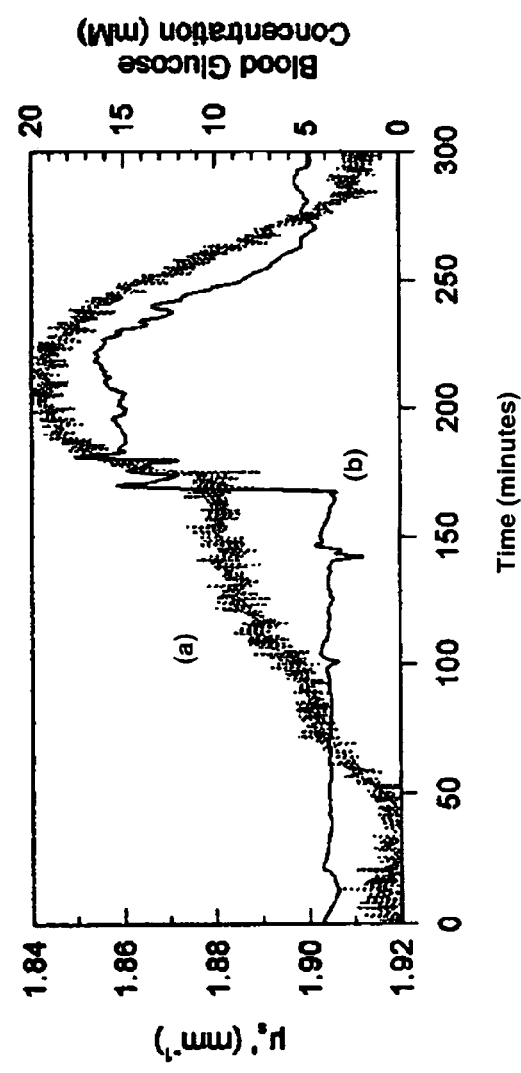
FIG. 2 illustrates the reduced scattering coefficient (a) and blood glucose concentration (b) over time for a diabetic subject (from Bruulsema et al., *Optics Letters,* Vol. 22, 190 (1997).
Figure 3:
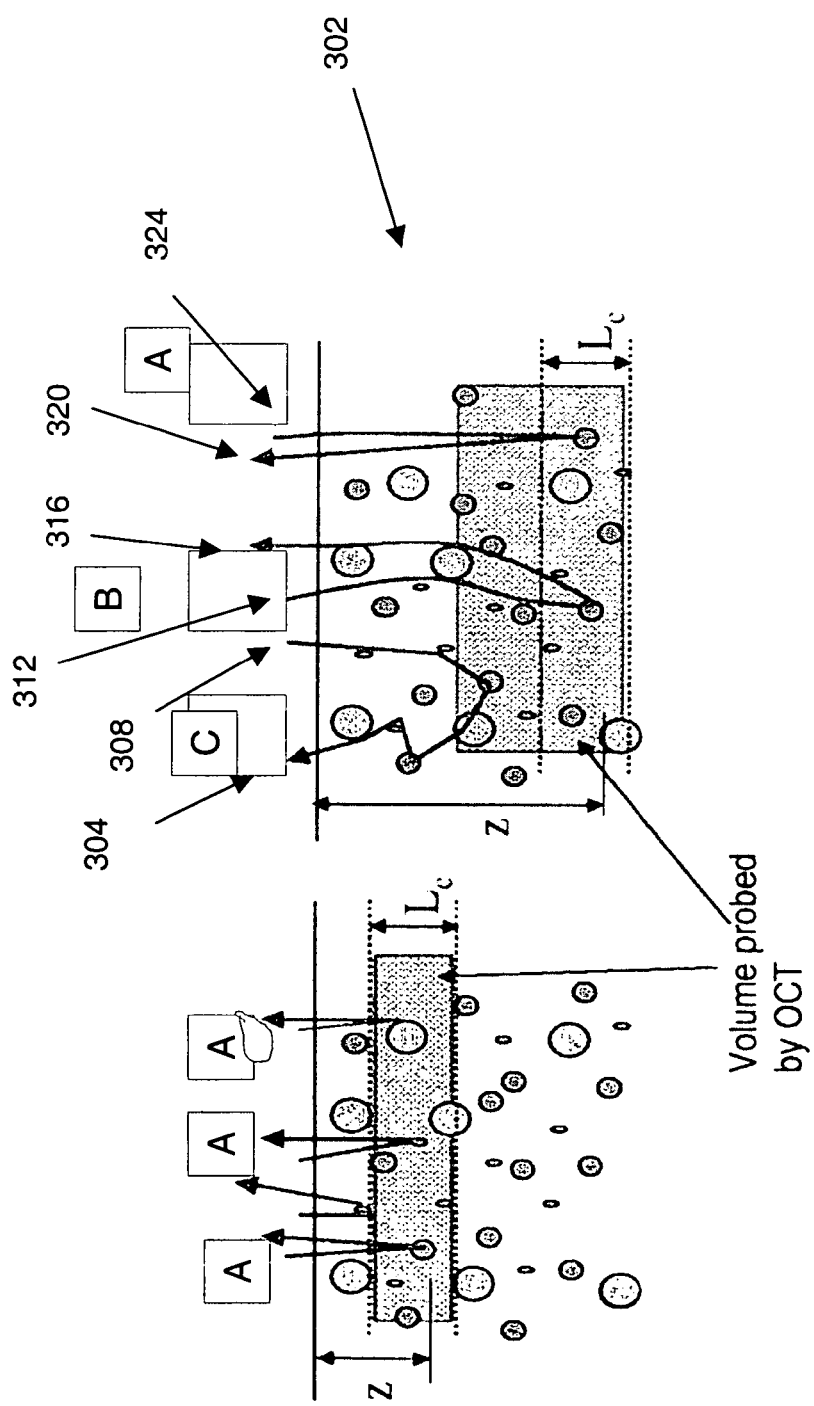
FIG. 3 depicts the effects of multiple scattering as a function of the targeted depth, z.

FIG. 3 illustrates how the multiple scattering contributions between incident photons in a diffusive medium or optically dense material such as a polymer dispersion or human tissue can depend on the targeted depth z in the material. The amount of multiple scattering contributions to the recorded signal depends not only on the depth value z but also on the coherence length $L_c$ of the source radiation and the optical characteristics of the medium between the interface and the targeted depth.

As illustrated in FIG. 3, probing the medium at a higher depth actually enlarges the volume probed in standard OCT (optical coherence tomography). The depth (z) probed by a source of light incident on the sample may be varied using different wavelengths of low coherent light or through the use of lenses 2012 and 2016 as illustrated in FIG. 20. In FIG. 3, the path or trajectory A of incident low coherent light injected at point 324 into the sample 302 and exiting the sample at 320 refers to a single backscattered signal. The path or trajectory B, for example incident low coherent light injected at point 312 into the sample 302 and exiting at point 304 refers to multiple forward scattered light exiting the sample 302. The path or trajectory C given by propagation of light injected into the material sample 302 at point 312 and exiting the sample at point 316 also refers to multiple forward scattered light. At higher depths, paths of types B and C become increasingly more probable adding their contribution to the background noise, attenuating the backscattered signal at the injection point, and decreasing both the axial and transversal resolution. Typically the greater the depth into the sample that is probed, the greater the noise. The complexity precludes a simple estimation of the multiple scattering background (noise level).

Figure 4:
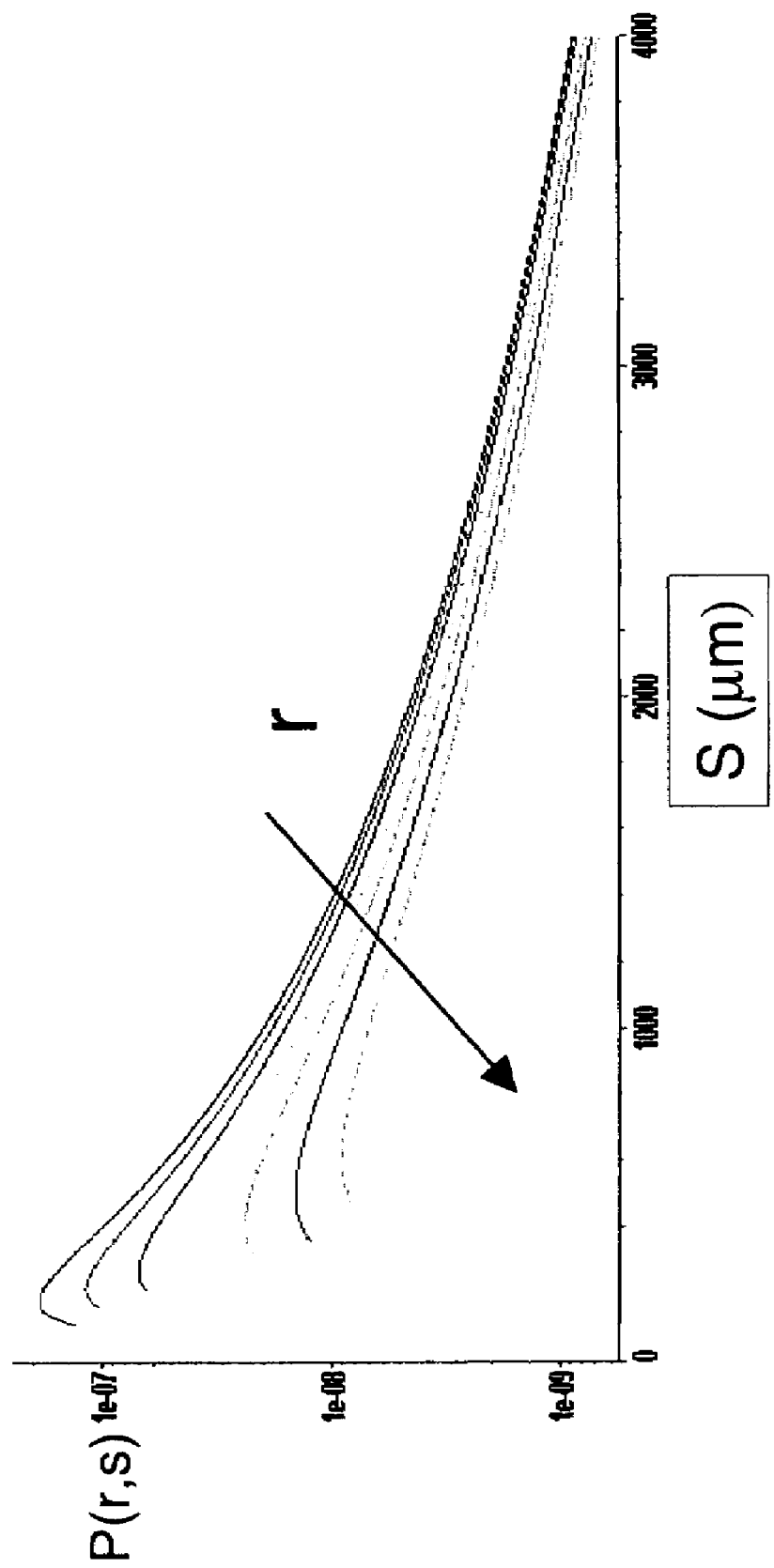
FIG. 4 is a graph of a numerical example where the photon probability distribution P(r,s) for various separation distances (r) are plotted as a function of optical pathlength (s) for increasing values of the separation distance (r) as indicated by the arrow.

The interferometric sensor of the present invention includes one or more sample arms probing a sample at different points from the light injection point, each sample arm having the same optical path length denoted by (s). The spacing, (r), between the light injection point and one or more sample arms to collect backscattered light from the sample is preferably chosen to provide a diffusion coefficient D (inversely proportional to the scattering coefficient $\mu_a$) and an absorption coefficients $\mu_s$ for light having a tortuous path in the sample and D and $\mu_s$ for light having a ballistic path or trajectory in the sample. For light having a tortuous path in the material, scattering and absorption contribute to the source light attenuation. For light having a ballistic path, attenuation of the light is predominantly caused by absorption of the source light by the sample. Different path lengths (s) for light interacting with the sample may be probed by the interferometric sensor through adjustment of the physical length, optical length, or optical delay of the reference arm of the interferometer. Backscattered light with the same optical path length from multiple points on a sample material is collected and coupled with light having the same path length from the reference arm. Interference between the reference arm light and sample light is detected and can be used to determine the pathlength distribution of photons for a number of different separation distance (r) over a range of optical pathlengths (s) as illustrated in FIG. 4.

When light strikes the boundary surface separating two media of different optical densities, some of the incident energy is reflected back as illustrated schematically in FIG. 5. This property is referred to as reflectance and by some authors as backscattering from the interface. The techniques used to measure this light falls under the broad definition of reflectometry. This is different from the backscattering of light that undergoes multiple scattering in traversing a trajectory 620 in particulate media or a composite media as illustrated in FIG. 6. It is important to realize this distinction between the single backscattering (specular and diffuse reflection) of light from an interface and the light backscattered from a system of scattering centers due to a multiple scattering process. Instruments that detect the position and strength of one inhomogenity, i.e., single-scattering in the back scattering direction, are those that rely on low-coherence optical interferometry (sometimes called white light interferometry).

Figure 10:
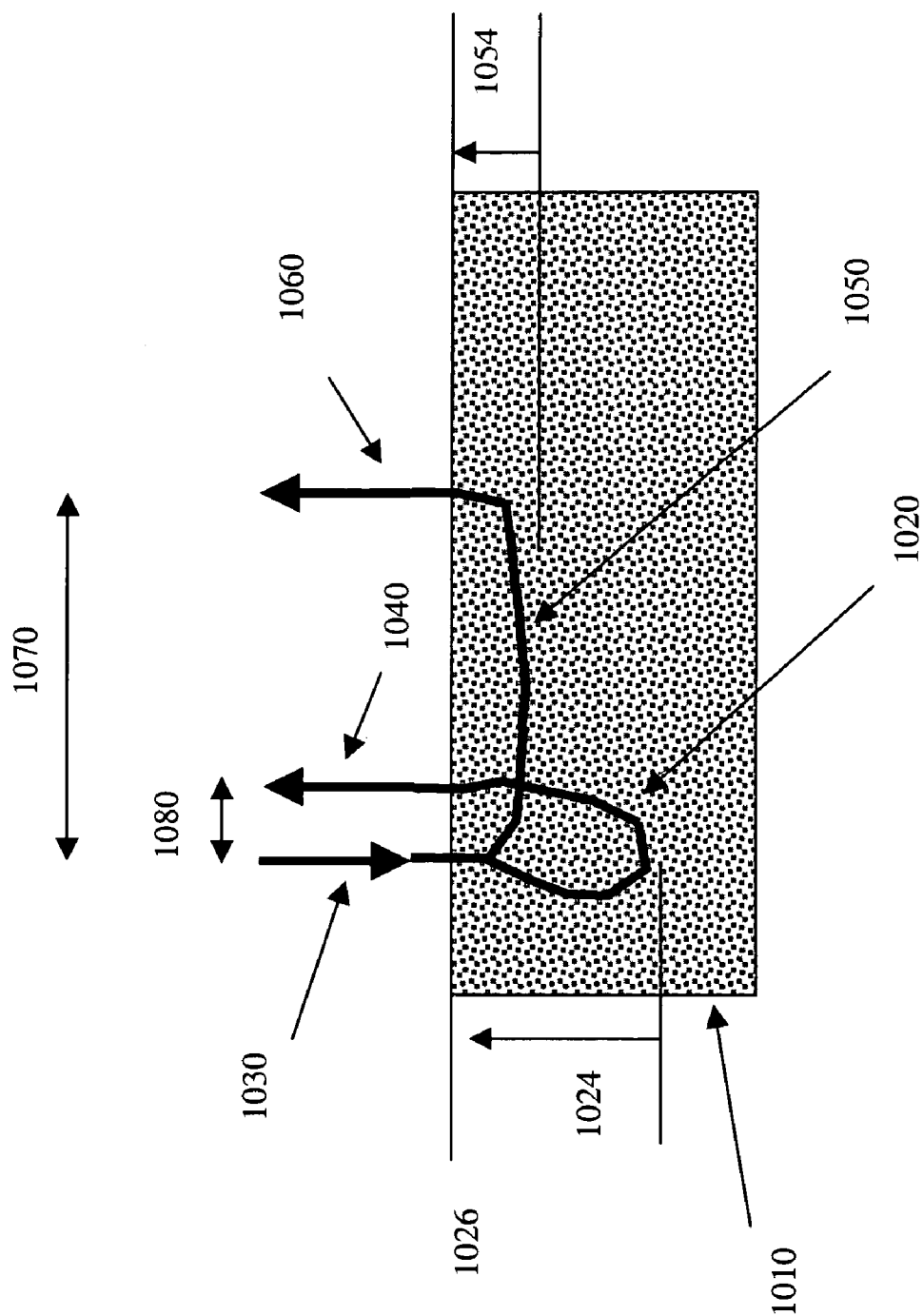
FIG. 10 illustrates various measuring geometries with variable distance between the points of injection and collection of optical radiation.

FIG. 10 illustrates a material sample 1010 injected with a source of light 1030 and backscattered light being sampled by collectors 1040 and 1060 from the sample. The two or more light collectors, 1040 and 1060, are capable of collecting and coupling the backscattered light from the sample with reference arm light having the same optical path length (s). The separation distance, for example (r1) 1070 or (r2) 1080, between the source light 1030 directed at a material 1010 and backscattered light detected from the material at 1060 or 1040 can be changed and used modify the trajectory of the light 1020 or 1050 through the sample 1010. The optical path length (s) or optical delay for light that includes the trajectory 1020 is maintained at the same length as trajectory 1050. Changing the separation distance between 1030 and 1040 (r2) or the separation distance between 1030 and 1060 (r1) the contribution of absorption and scattering to the backscattered light from the sample can be determined. For example, light from a low coherent source (not shown) can be directed or injected into the sample material 1010 from 1030. A first trajectory, 1020 whose optical path length (s) is determined by the reference arm (not shown) probes the sample to a depth 1024 from the top 1026 of the sample 1010. A second trajectory 1050 with the same optical path length (s) determined by the same or a different reference arm probes the sample to a shallower depth 1054 from the top 1026 of the sample. Light of trajectory 1020 is both absorbed and scattered by the sample, light of trajectory 1050 is dominated by absorption, it has a smaller scattering component, than light of trajectory 1020 because light of trajectory 1050 penetrates the optically diffuse sample to a shallower depth than light of trajectory 1020.

Figure 11B:
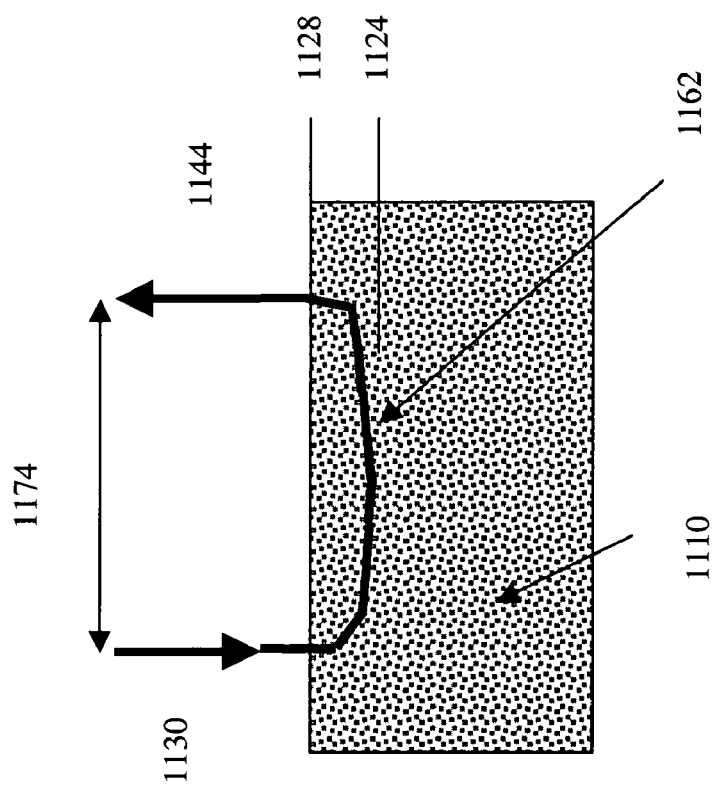
FIG. 11B illustrates that for a large separation distance (r) between injection and light collection points, light with the same optical path length (s) as in 11A develops primarily along the surface where the distance between the ending points is sufficiently large; the separation distance (r) between injection and light collection points may be used to control the depth and trajectory of light in the material.
Figure 11A:
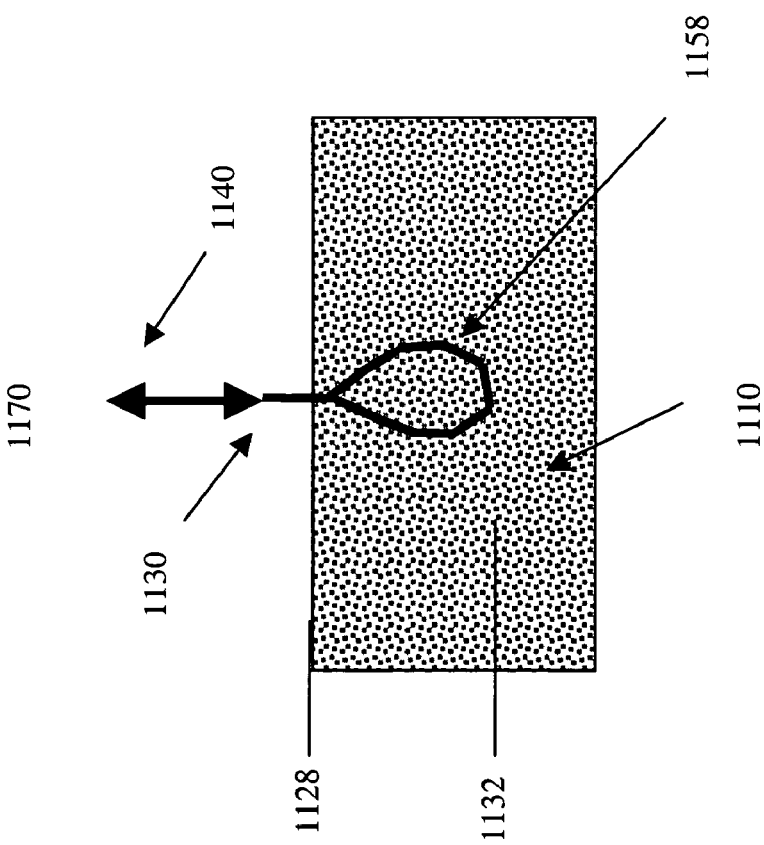
FIG. 11A illustrates that for a give for a given optical path length (s), a small or zero separation distance (r) between injection and light collection points causes light to penetrate into the sample.
Figure 12:
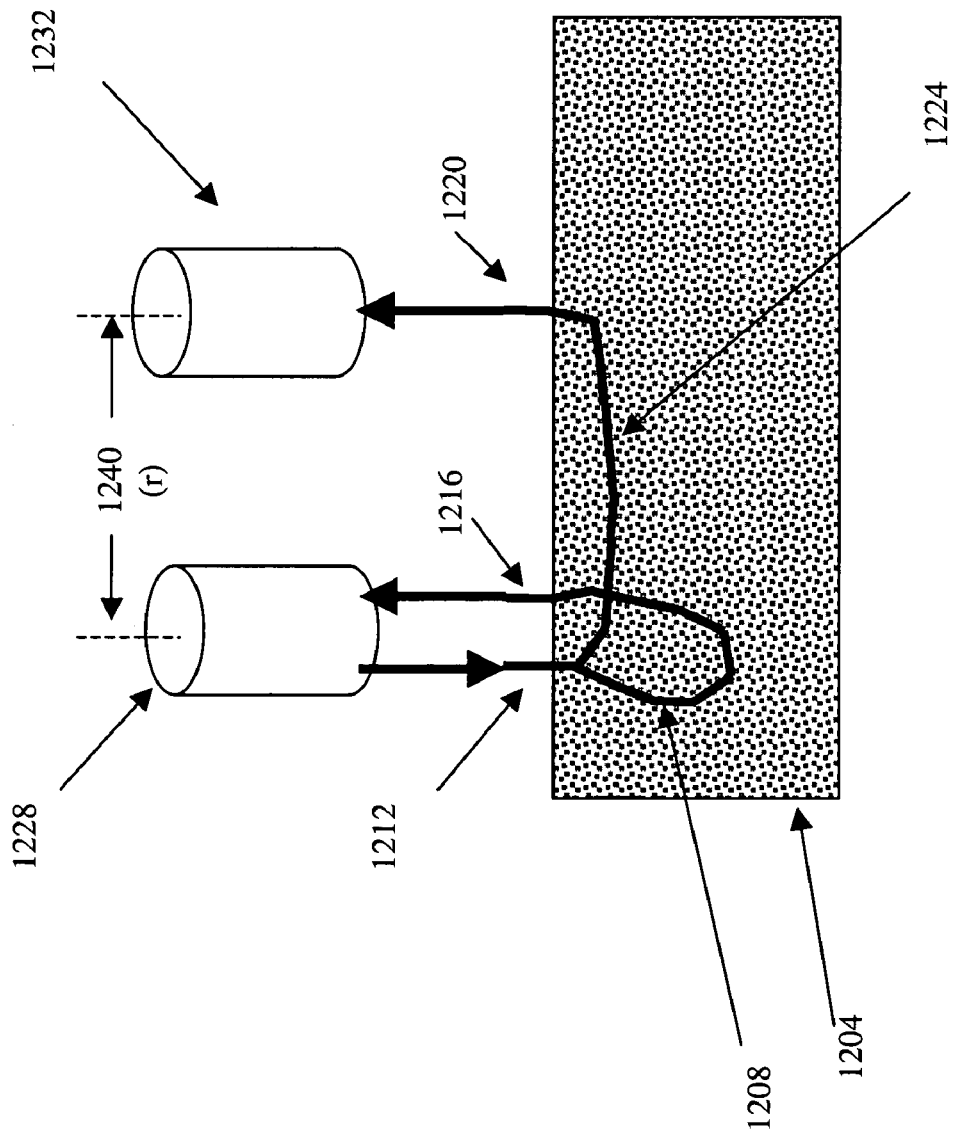
FIG. 12 illustrates a transceiver and light collector that can be used to probe a sample and measure the same path length (s), but different trajectories, for various separation distances (r) between the transceiver and detector.

As illustrated in FIG. 11A, source light 1130 directed into the material 1110 has an optical pathlength (s) that include light with a trajectory 1158 and where the backscattered light is collected by 1140. The separation distance (r1) between the source 1030 and light collector 1140 is represented by 1170 and in this case is zero. The trajectory probes the sample to a depth 1132 from the top surface 1128 of the material 1110. An interferometer where one arm is a transceiver as illustrated in FIG. 12 could be used to inject light and detect light to give a trajectory 1158. As shown in FIG. 11B, source light 1130 injected into the sample 1110 and having a trajectory 1162 with optical pathlength (s) can be collected by 1144 from the sample. The trajectory 1162 probes the sample to a depth 1124 from the top surface 1128. The separation distance (r2) between the source 1130 and light collector 1144 is given by 1174. The maximum distance 1174 between the light injection and collection can vary depending upon variables including but not limited to the attenuation of the light by the material being examined, the power and wavelength of the light source, the sensitivity of the detector, and the concentration of analyte or material being examined for. Preferably the separation distance is less than about 1 centimeter.

In FIG. 11A, the trajectory 1158 will be determined by both scattering and absorption coefficients while in FIG. 11B the trajectory 1162 that the photons that propagate along the ballistic trajectory will mostly be influenced by the absorption of the sample. In embodiments of the present invention the optical sensor, one can independently adjust the distance (r) between the ending points of the trajectory (source and detection points) and set the length of the photon pathlength (s) by the reference arm. As shown in FIG. 12 an optical fiber 1228 from a first interferometer can act as a transceiver and may be used to direct light from a source (not shown) at point 1212 into the sample 1204. Backscattered light with a trajectory 1208 and an optical path length (s) determined by the reference arm of the interferometer may be collected by the transceiver 1228 at point 1216 and further coupled with the reference arm light. The point 1212 and 1216 are shown separated (r1) for clarity. Practically 1216 is within the region of the diameter of the fiber, the channel waveguide, or source beam for a free space device. A second light collector 1232, which may optionally be a transceiver, forms part of an interferometer having the same path length (s) as the transceiver 1228 and can be separated from the transceiver 1228 by a distance (r2) of 1240. The light collector 1232 can be used to measure backscattered light at point 1220 from material 1204 having a resultant trajectory 1224.

FIG. 13 illustrates fiber optics-based sensor in an embodiment of the present invention with fixed delay lines that set the optical path length. An optical coupler 1308 directs light from source 1316 into fiber optic 1306 and into sample 1304. Light backscattered from the sample with trajectory 1302 is collected at fiber optic light collector 1324. The interference between the reference arm light with retroreflector 1320 and the scattered light collected at 1324 is detected by detector 1328 and converted into a electrical signal proportional to the intensity of interference. The distance between 1306 and 1324 determine the separation distance (r1) for the first interferometer. In the second interferometer which has the same optical path length (s) as the first interferometer, optical coupler 1348 directs light from source 1332 into optical fiber 1334 and is injected into the sample 1304. Backscattered light from the sample is collected in optical fiber 1350 light collector and the separation distance (r2) defined by the distance between 1334 and 1350. The interference between the reference arm light with retroreflector 1336 and the scattered light collected at 1350 is detected by detector 1344 and converted into a electrical signal proportional to the intensity of the interference. The electrical signal from detector 1344 and 1328 can be processed further to determine the coefficients of absorption and scattering and correlated to the concentration of an analyte in the sample.

A fiber optic based sensor with adjustable delay lines is illustrated in FIG. 14. The sensor includes adjustable delay lines using triple reflectors 1420 and 1428 and a common low coherent light source 1424. Light from the source 1424 can be injected into a region of the sample 1404 through fiber optic 1446. Backscattered light from the sample 1404 is collected at two different points or regions separate from the region where light is directed into the sample. The light is collected by light collectors 1412 and 1450 positioned to give equal length trajectories 1402 and 1454 respectively. The separation distance (r1) between 1412 and 1446 and the separation distance (r2) between 1450 and 1446 being different. The optical path length (s) or optical delay for each interferometer being the same and determined by the position of the triple reflectors 1420 and 1428. Detector 1416 measures the interference between reference arm light 1418 and collected backscattered light 1412 combined together by coupler 1408, detector 1432 measures the interference between reference arm light 1430 and collected backscattered light 1450 combined by coupler 1442.

Figures 15, 16:
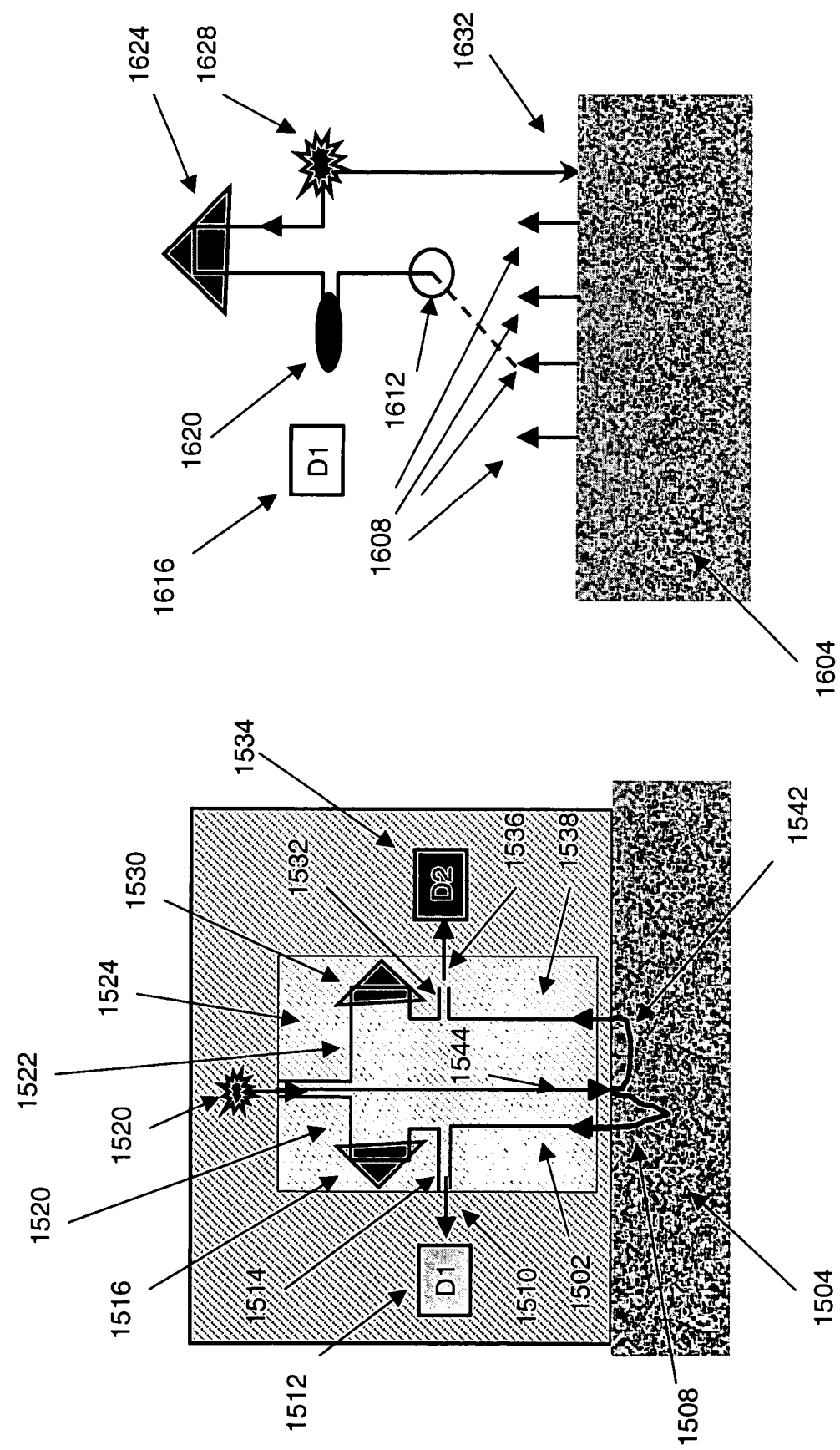
FIG. 15 illustrates an integrated optical sensor device for characterizing a material that can have fixed or adjustable delay lines.
FIG. 16 shows a compact fiber optic-based device that may be used to independently characterize the absorption and scattering coefficients of a material that includes one interferometer but different separation distances between the injection and collection points; the different separation distances are generated using a fiber optic switch to address optical fibers, transceivers, or integrated waveguides at fixed distance from the source injection point.

FIG. 15 illustrates integrated optics with fixed or adjustable delay lines. Waveguide 1544 formed on substrate 1524 interconnects a low coherent light source 1520 with the a diffuse, optically dense sample 1504. The low coherent light source may be include one or more multiple quantum well emitters, each emitter having a different center wavelength. Waveguides 1502 and 1538 collect light backscattered from the sample 1504 and propagate it to detectors 1512 and 1534 respectively. The separation distance (r1) between 1502 and 1544 selected to provide a trajectory that probes into the sample, and the separation distance (r2) between 1538 and 1544 selected to provide a trajectory 1508 that probes nearer the surface of the sample, the optical path length (s) or delay for the paths that include trajectories 1508 and 1542 for each interferometer being the same and determined by the delay line structures 1516 and 1530. Detector 1512 measures the interference between reference arm light 1514 and collected backscattered light 1502 combined together by integrated coupler 1510, detector 1534 measures the interference between reference arm light 1532 and collected backscattered light 1538 combined by integrated coupler 1536.

Information about the scattering and absorption coefficients of a material 1604 as illustrated in FIG. 16 can be obtained by measuring individually the collected backscattered light from a plurality of light collectors 1608 that is combined with reference arm 1622 light using coupler 1620, and the intensity of interference detected by detector 1616. In FIG. 16 each light collector 1608 has a different separation distance ($r_1$, $r_2$, $r_n$ where n is an integer 1 through the number of collectors 1608) from the point 1632 where a low coherent source light 1628 is injected into the optically dense material 1604. A fiber optic switch 1612 permits sequential sampling of backscattered light collected from each of the light collectors 1608. Although the sensor can include a mechanism that moves or scans the position of a light collector relative to the region where light is injected by a transceiver into the sample, the use of multiple light collectors at fixed positions enables multiple separation distances (r) to be sampled within a small area of the sample without the need for positioning mechanisms to adjust the separation distance. This type of device is advantageous for use in housings where small size is important such as in an endoscope, catheter, or borescope. Each of the light collectors 1608 measures the backscattered light has the same optical path length (s) or delay determined by the reference arm. In an alternative embodiment the light injector 1632 and the light collectors 1608 may be configured as transceivers (not shown) to provide different separation distances between the transceivers but sampling backscattered light from the sample having the same optical path length. The optical switch may be used to select two or more transceivers.

Figure 17:
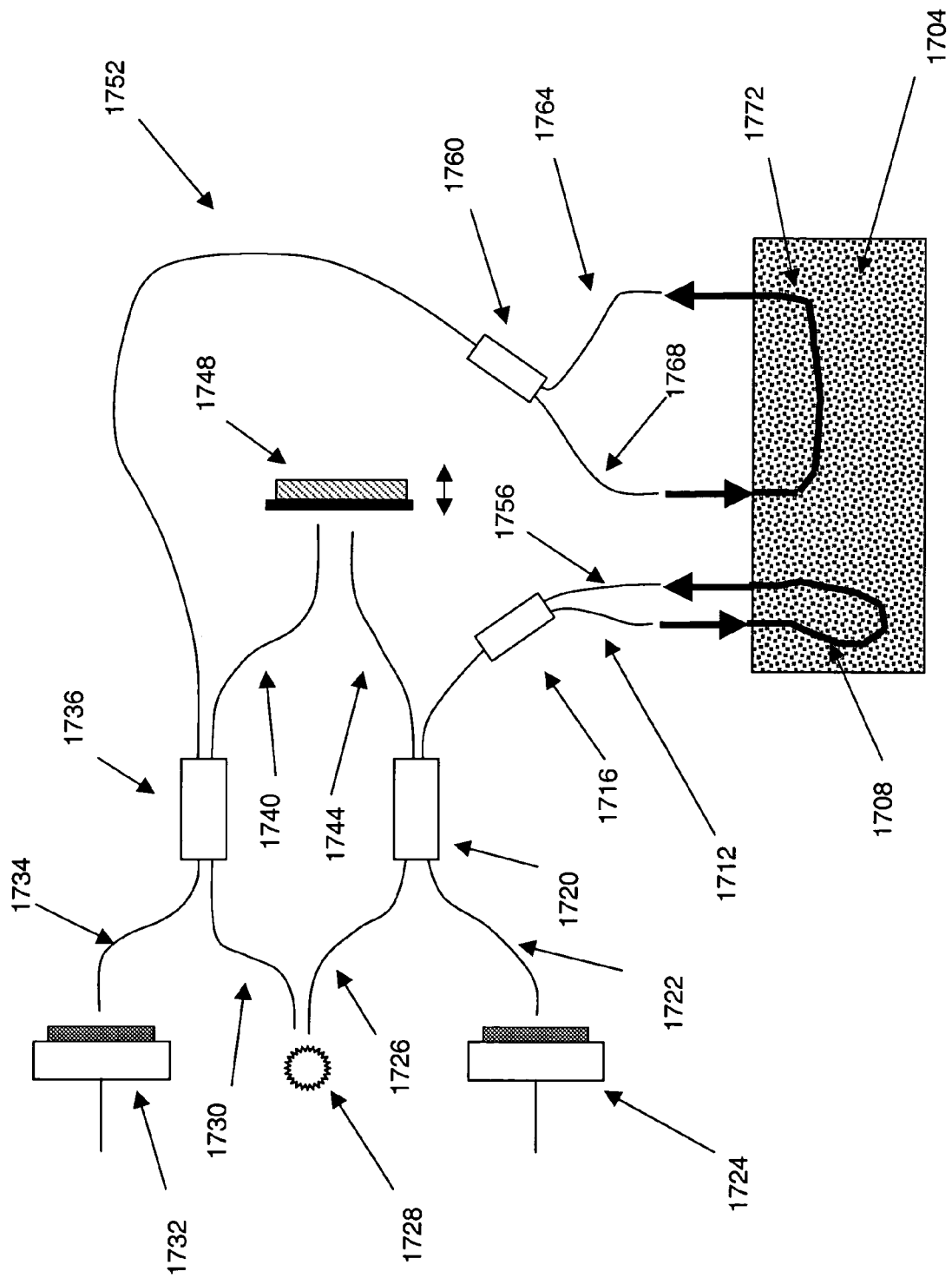
FIG. 17 shows a fiber optic device that includes a single low coherent light source, one or more detectors, and a common reference arm to set the optical path length for the one or more detection points.

FIG. 17 illustrates a combination of free space and fiber optic components that may be used in an embodiment of the present invention. The low coherent source light 1728 is shared and injected into the sample through optical fibers 1712 and 1768. Backscattered light from the diffuse sample material 1704 is collected by light collectors 1756 and 1764. The separation distance (r1) between optical fiber 1712 and light collector 1756 gives trajectory 1708 having a torturous path while the separation distance (r2) between optical fiber 1768 and light collector 1764 provide a trajectory having a less torturous and a more ballistic like path through the sample. Backscattered light from the sample collected by 1764 is combined with reference light 1740 with optical path (s) set by adjustable mirror 1748 in coupler 1736. The interference detected from the combined light is detected by detector 1732. Backscattered light from the sample collected by 1756 is combined with reference light 1744 with optical path (s) set by adjustable mirror 1748 in coupler 1720. The interference detected from the combined light is detected by detector 1724. The output from the detectors 1732 and 1724 can be further conditioned, converted or filtered and used as input for a processor (not shown) to determine the diffusion coefficient D and absorption coefficient $\mu_a$ of the material 1704 by applying Eqs. (2-4). The concentration of an analyte in the material may be correlated to the diffusion coefficient D and absorption coefficient $\mu_a$ of the material and used to monitor the concentration of the analyte in samples of the material.

In both fiber optic design and the integrated photonic devices, the polarization properties of incident and collected light can be independently controlled permitting a polarization-resolved detection for enhanced specificity. This capability is exemplified in FIG. 18 for a fiber optic based sensor, however a similar device could be fabricated as an integrated device. FIG. 18 illustrates polarization resolved interferometers. FIG. 18 illustrates two different light trajectories 1854 and 1852 in the sample 1804 provided by making the separation distance (r1) between polarized light 1846 injected into the sample 1804 and (r2) for light collectors 1812 and 1850 different. Polarizing elements 1818 and 1830 are positioned in the reference arms, polarizing elements 1808 and 1840 in the sample collection arms and polarization element 1848 positioned between the sample and common low coherent light source 1824.

Surface coupling effects, $z_e$ may be minimized or eliminated through use of the methods of the present invention as described in Eqs (1-4). This effect may also be minimized Sensor devices of the present invention may also minimize surface coupling effects by including dual low coherent light sources 1912 and 1920 as shown in FIG. 19. In this case, two lights through light splitter 1928, one tightly focused 1936 and another one significantly broader 1906 by lens 1932 performs the sample illumination. In this way, by examining both coupling situations one can reduce the dependence of light coupling on the properties of the surface. The two lights can be part of two independent interferometers that share the same measurement axis. As shown in FIG. 19, one can use lights in different polarization states, for example polarizer element 1916, to distinguish between the radiation originating from one light source or another. Using lights of slightly different spectral composition, for example low coherent light sources having a different central wavelength is another way to discriminate between radiation originating from lights with different spot sizes and also provides an independent way to probe different depths within the sample 1904.

Another physical way to isolate the effect of the coupling interface is to have the source of radiation placed at a certain depth underneath the surface. As illustrated in FIG. 20 a dual focused light, for example light 2014 focused by positive (one that brings collimated light to a focus, as per light rays 2024) lens 2012 at point 2032 just below the surface of material 2004 and light 2024 focused by lens 2012 at a point 2008 within in the material 2008. In this case for 2008 to be at a greater focal depth than 2032, the rays 2014 that form spot 2008 diverge, at least slightly compared to the collimated light 2024, as indicated. Use of polarization element 2016 can also be used to inject light into the sample thereby overlapping radiation with different states of polarization (or different spectral composition). The analysis of the scattering and absorption processes originating in the two different points can be used to limit in influence of the coupling interface. The optical paths originating from the depth of the sample 2006 will be less affected by the coupling interface. A relative interpretation of the results can also be used to isolate the interface effects. Such optical heads can help to obtain a better separation of the ballistic component 2036 along the surface minimize surface coupling effects.

A low coherent light source can also be injected within the diffusive material like skin by focusing the light into the material with an axicon type geometry as illustrated in FIG. 21. In this case, a compact optical head 2124 can be built which injects most of the light 2120 in the depth 2116 of the sample 2104. Axicon optical heads can be practically manufactured using both diffractive or refractive techniques. These designs again are not limited to fiber optic sensors but can also be implemented in the packed, monolithic sensors.

Figure 22:
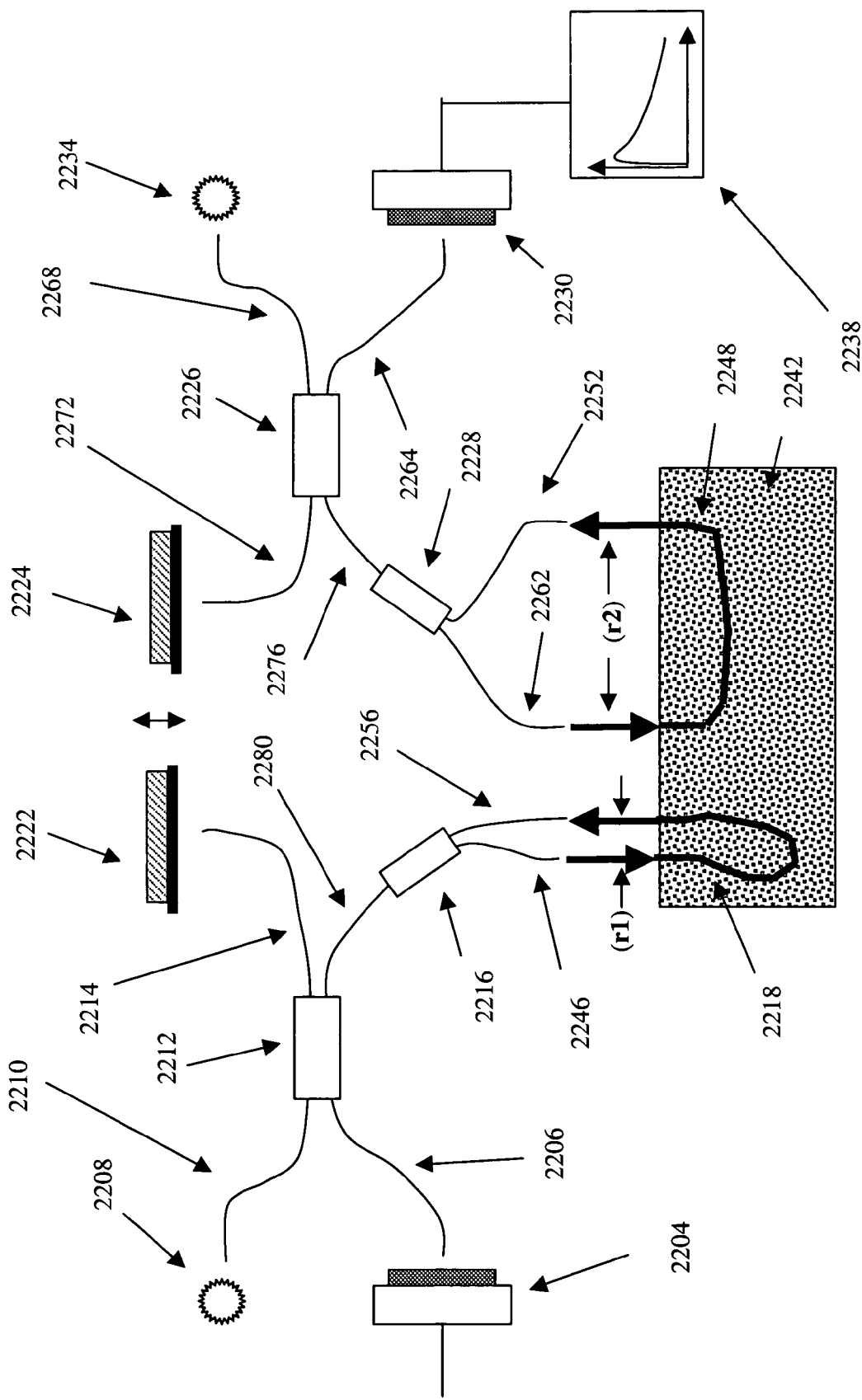
FIG. 22 illustrates an embodiment of the present invention that utilizes fiber optics.

FIG. 22 illustrates an embodiment of the present invention where independent optical fiber based interferometers are used to probe the an optically dense sample 2242. Low coherent light from a source 2208 is propagated by optical fiber 2210 to coupler 2212 where a portion of the light is directed to reference arm 2222 by optical fiber 2214. Another portion of the light from the coupler 2212 propagates to the sample through coupler 2216 and fiber 2246 where it is injected into the sample 2242. Light having trajectory 2218, backscattered light, is sampled by light coupler 2256 separated from the injected light by a distance (r1) and combined with reference light through fiber 2280 in coupler 2212. Detector 2204 measures the intensity of interference between the backscattered light collected by 2256 and the reference arm light. Low coherent light from another source 2234 is propagated by optical fiber 2268 to coupler 2226 where a portion of the light is directed to reference arm 2224 by optical fiber 2272. Another portion of the light from the coupler 2226 propagates to the sample through coupler 2228 and fiber 2262 where it is injected into the sample 2242. Light having trajectory 2248, backscattered light, is sampled by light coupler 2252 separated from the injected light by a distance (r2) and combined with reference light through fiber 2276 in coupler 2226. Detector 2230 measures the intensity of interference between the backscattered light collected by 2252 and the reference arm light. The optical path ($s_o$ or s) for light in the two interferometers is the same and the output signals from detectors 2204 and 2230, illustrated by 2238 for detector 2230, can be used as input to a processor (not shown and after conversion, filtering or conditioning if necessary) to determine the diffusion coefficient D of the material and the absorption coefficient $\mu_a$ of the material 2242. The diffusion coefficient D of the material and the absorption coefficient $\mu_a$ of the material may be related to the type of material or to a concentration of an analyte in the material. One or more of the components illustrated may be contained in a chemically inert housing with suitable optically transparent windows and used to characterize various materials.

Figure 23:
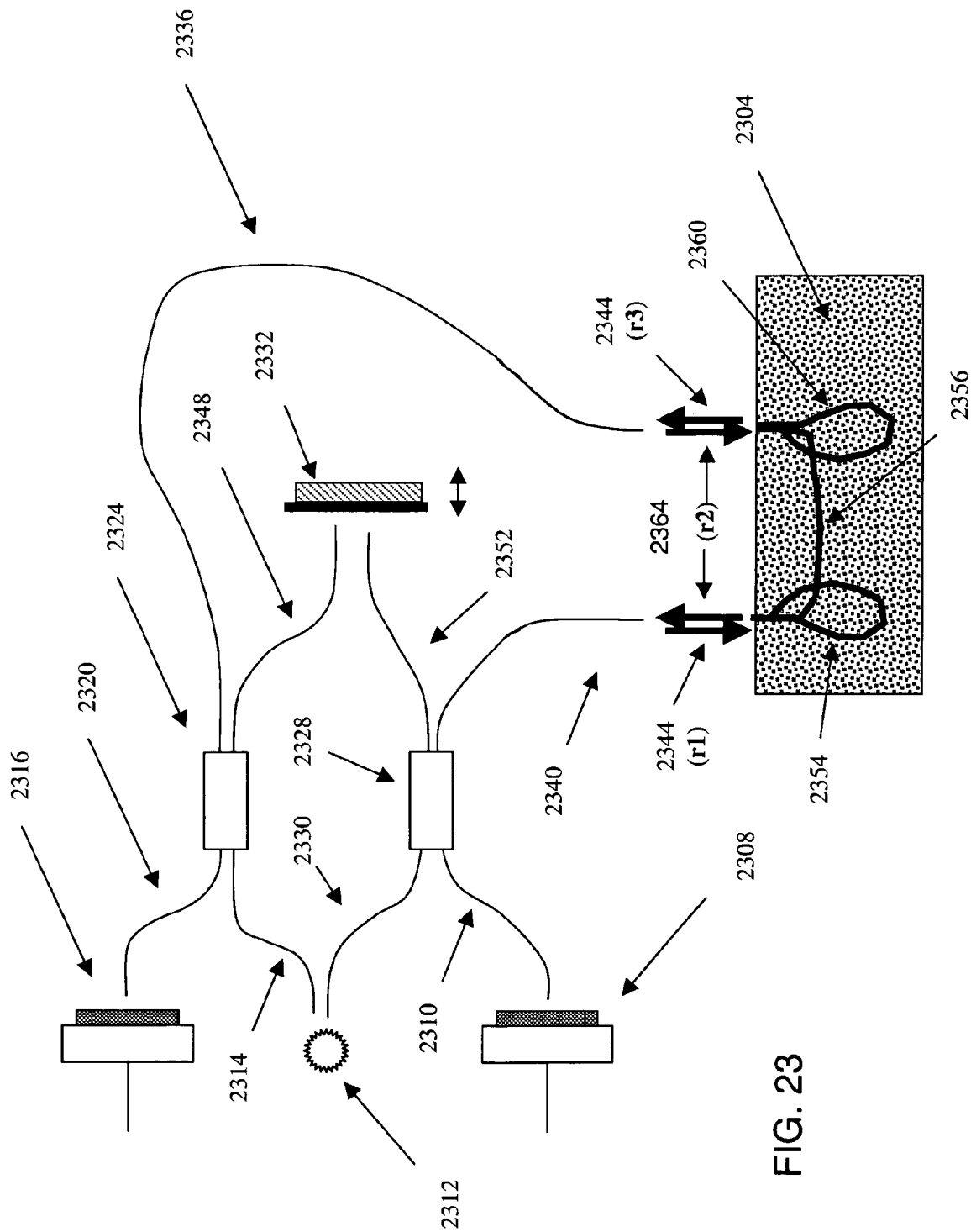
FIG. 23 illustrates a fiber optic embodiment of the present invention wherein an optical fiber acts as a transceiver.

A more compact design of the sensor illustrated in FIG. 22 can also be implemented as shown in FIG. 23, by having the two interferometers share the same light source 2312 and the same reference arm 2332. This would permit simultaneous detection of light scattering along the surface trajectory 2356 and the depth trajectory 2354 of the diffuse material 2304. Optical fiber 2340 acts as a transceiver with (r1) represented by 2344 being essentially zero in this region and optical fiber 2336 acts as a transceiver with (r3) essentially being zero. The separation distance (r2) between light injected to the sample 2304 by optical fiber 2340 and optical fiber 2336 can be varied. Backscattered light collected by transceiver 2340 is combined with reference arm light by coupler 2328 and the intensity of interference detected by detector 2308; backscattered light collected by transceiver 2336 is combined with reference arm light by coupler 2324 and the intensity of interference detected by detector 2316.

Figure 24:
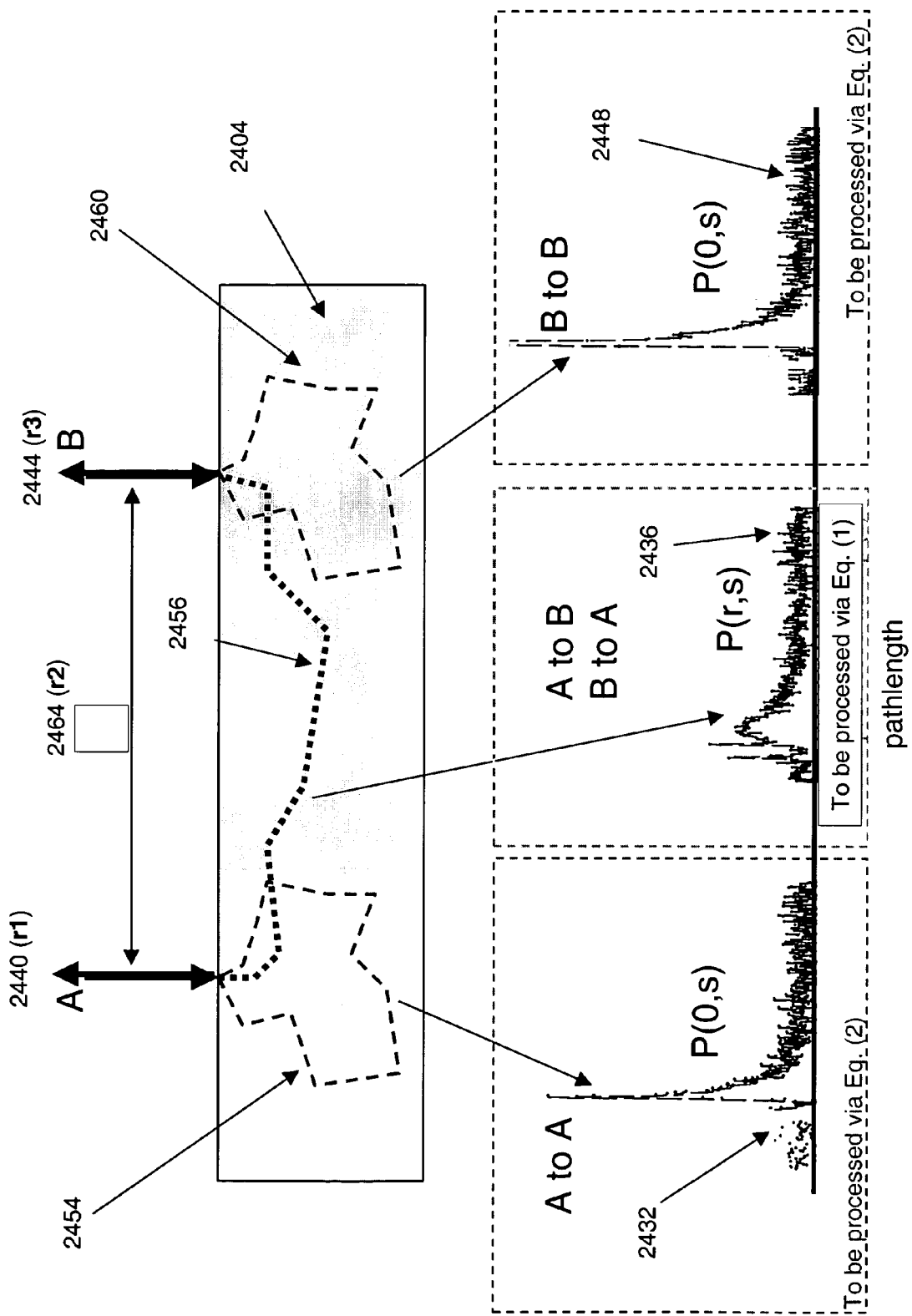
FIG. 24 illustrates an embodiment of the present invention utilizing multiple transceivers to independently determine the absorption and scattering coefficients of a sample.

FIG. 24 illustrates in more detail an embodiment of the present invention where two transceivers 2440 and 2444 are used to inject light into an optically dense material 2404 and where each transceiver collects backscattered light from the sample 2404. The transceivers are separated by a distance (r2) denoted by 2464, and may be but are not limited to optical fibers, waveguides, or a combination of these. Because light is injected and detected by the transceiver 2440 at essentially the same point on the sample 2404, the separation distance (r1) is essentially zero; likewise light injected and detected by the transceiver 2444 is also essentially the same point and the separation distance (r3) is also essentially zero. The photon pathlength distribution for the trajectories 2454 and 2460 may be determined using Eq. (2) vide infra; and the photon path length distribution for trajectory 2456 may be determined using Eq. (1) vide infra. The trajectories 2454, 2456, and 2460 each have the same optical path length (s) or delay as the reference arm. The trajectories 2454 and 2460 are more tortuous due to scattering by optically dense sample 2404 than light path 2456 which has a more ballistic like trajectory. The photon distribution for source light injected at A and detected at A is shown as a function of path length in trace 2432. The photon distribution of light injected at B and detected at B is similar to that for the A to A trajectory as shown by the trace 2448. Light injected at A and detected at B and light injected at B and detected at A by the transceivers 2440 and 2444 gives the photon distrubution as a function of path length as illustrated by trace 2436.

The interferometric devices in embodiments of the present invention, for example but not limited to those illustrated in FIGS. 13-23, may be enclosed in a housing. The housing can provide physical support for waveguides and fibers, chemical protection, and features which provide irrigation and cleaning of lens and windows. FIG. 25 illustrates a non-limiting housing for a sensor of the present invention. The housing can include wall 2504, optical fibers or waveguide transceivers 2508 and 2512 for injecting light and collecting backscattered light from a sample through a transparent window 2516 mounted integrally to the housing which may have an optional antireflective coating. The window 2516 may be used to contact the sample 2520 and to inject light from the transceivers 2508 and 2512 into the sample 2520. Light backscattered from the sample 2520 is collected by the transceivers through the window 2516. In another embodiment shown in FIG. 26, a housing having side walls 2664, an endcap 2660 mounted or integrally formed with the wall 2664, transparent windows 2652 and 2656 mounted to the housing wall 2664 and fiber optic or waveguides 2640 and 2644 each acting as a transceiver for injecting low coherent light from a source (not shown) and collecting backscattered light from the sample for coupling with reference arm light (not shown). The windows contact the sample 2643 surrounding the housing. Trajectories 2688 and 2676 have a separation distance (r1) of zero, trajectory 2672 has a separation distance (r2) given by the difference between the points of contact of the fibers or waveguides with the housing windows. The trajectories 2672, 2676, and 2688 have the same length through the sample and the same optical path lengt (s) or optical delay which can be adjusted by the reference arm(s) of the interferometers (not shown). A device as shown in FIG. 25 may be used to probe the surface of a material or a tissue like skin. A device as shown in FIG. 26 may be used to probe the surface of a conduit, or a body cavity like the colon or esophagus.

The sensor and method in various embodiments may be used on a variety of diffuse or optically dense materials including but not limited to polymers, composite engineering materials, tissues, and skin. Further, the sensor of the present invention can be used to characterize the outer and inner surfaces of these materials. For example, the sensor of the present invention may be configured in a housing as illustrated in FIG. 25 and FIG. 26 for use as an endoscope, catheter, or as a borescope to characterize materials residing on exposed and open surfaces and on closed surfaces such as but not limited to conduits, cavities, and bores in various biological and industrial applications. While the description of the invention may be made with particular reference and example to biological tissues like skin and the characterization of analytes present in the interstitial fluid of skin, the invention is not the intent to limit the applications so described therein. Furthermore although the term endoscope is used, this invention directly relates to guidewires, catheters, and imaging with probes placed through trocars.

The present invention is related to an interferometric optical sensor. Such sensors have been used in industrial process control to determine the size and distribution of particles in a medium as disclosed in U.S. Pat. Nos. 6,525,823 and 6,256,103 the contents of which are incorporated herein by reference in their entirety.

Various interferometer configurations may be used in the sensor of the present invention. Preferably each interferometer is capable of providing path length resolved backscattered intensities from one or more points on a sample utilizing a low coherence source. Examples of interferometers that may be used include but are not limited to free space Michelson and free space equivalents of a Mach-Zehnder interferometer, fiber optic Michelson and Mach-Zehnder interferometers, and combinations of free space and fiber optic versions of these. One example is a fiber-optic Michelson interferometer is shown in FIG. 22 where light from a source 2208 propagates through a single mode fiber 2210 to an evanescent-mode coupler 2212. The coupler transfers a part of the light power to another fiber 2214 which is propagated to the reference mirror 2222 or arm of the interferometer, while the other part of the light power is propagated to the sample 2242 by optical fiber 2246.

Interferometers of the present invention may include those made using integrated optics technology. These sensors may include waveguides, fixed or adjustable delay lines, modulators, switches, multiple quantum well emitters, and other optical functions formed in or on a substrate using thin film and microfabrication techniques including but not limited to lithography, physical and chemical vapor deposition, as well as chemical and ion etching. Integrated optical devices including interferometers in embodiments of the present invention may be formed with materials including but not limited to polymers, ceramics, glasses, dielectrics, metals, and semiconductors. The integrated sensors of the present invention may fabricated and designed to have no moving parts. Using integrated optics manufacturing and design, a robust, monolithic sensor can be designed that can be placed in direct contact with the skin and contains all the necessary optical elements. The sensors in embodiments of the present invention can also be made using a combination of optical fiber technology, integrated optics including waveguides and fixed or adjustable delay lines, and free space device components.

Light sources useful in the present invention include those which are capable of penetrating material samples and providing torturous as well as ballistic light trajectories in the sample. Examples of such light sources include low coherent light sources or multiple low coherent light sources with different center wavelengths whose outputs have been combined. The source may emit in the near infrared and infrared, have a short coherence length, and have high irradiance for penetrating deep into the sample. Preferably for probing tissue, the low coherent light sources have wavelengths in a range of from about 600 to about 1800 nm. Examples of sources include but are not limited to edge emitting LEDs, superluminescent diodes, multiple quantum well light emitting diodes, mode locked Ti:Al$_2$O$_3$ laser, and superfluorescent optical fibers. One or more light sources having the same or a different wavelength may be used or one or more multiple quantum well devices may be formed on a single substrate to provide multiple wavelengths. The penetration of light into a material sample, preferably a tissue sample can vary with the wavelength and power of the of source light used, use of optical circulators, coupling losses and component attenuation of light, and the type of material being scanned. As an illustrative example for the sensor depicted in FIG. 23, light sources 2312 and may be one or more sources having multiple center wavelengths. In use the sample 2304 may be illuminated by a low coherent light source with a center wavelength of for example 1300 nm and the diffusion coefficient D and absorption coefficient $\mu_a$ determined at 1300 nm. Subsequently the sample can be characterized by light from source 2312 of a different wavelength such as 800 nm or 1800 nm and the diffusion coefficient D and absorption coefficient $\mu_a$ determined at these wavelengths. The light wavelength providing the best correlation with the concentration of an analyte in the sample may be selected for further use characterizing other samples of 2304.

Couplers, light splitters, or light combiners refer to components in an interferometer that can be used to both split the optical power of a low coherent light source for propagation through reference and sample arms of the interferometer and that can also be used to combine backscattered light from the sample with light from the reference arm. A variety of couplers, light splitters, or light combiners can be used including but not limited to an evanescent-mode coupler, a fiber coupler, a prism, a lightsplitter cube or light splitter plate. Without limitation, various types of couplers, splitters, or combiners alone or in combination can be used in sensors of the present invention. A retro-reflector is a device which may be used in embodiments of the present invention that reflects radiation (as light) so that the paths of the rays are parallel to those of the incident rays and can include but is not limited to mirrors and triple reflector cubes.

Sample light collectors are used to gather backscattered light from the sample illuminated by the low coherent light source. The light collectors can include but are not limited to optical fibers, mirrors, waveguides, or combinations of these including one or more lenses. In some cases the sample light collector also provides source light to the sample and functions as a transceiver. One or more sample light collectors, transceivers, or a combination of these may be used in an interferometer of the present invention. An example of a transceiver 1228 and a light collector 1232 used to characterize a sample material 1204 is illustrated in FIG. 12.

Some embodiment of the present invention allow for independent adjustment of the optical path length, optical delay, physical length, or any combination of these in each sample collector arm such that in one sweep of the reference arm one can collect all the interference signals provided by all the collectors. The physical length, optical length, or optical delay of the reference arm of the interferometer in the sensor may be fixed or adjustable.

The optical path length (s) or optical delay of the reference arm may be changed by scanning the reference arm. Preferably the path length or optical delay can be changed over a large enough distance to accommodate tortuous trajectories in optically dense materials. Different optical path or optical delays may be achieved by adjustment or scanning the reference arm. The reference arm may include but is not limited to a mirror, triple reflectors or retroflectors mounted on a stage and driven by a dc motor or voice coil. The reference mirror or retroflector and the sample objective lens may be placed on the same stage. Scanning may be achieved using linear translation, piezo-actuated optical delay lines, or movement of the tip of a sample fiber conducting the source light to an objective lens. The path length or optical delay of the reference light may be changed in a known manner in order to provide a known reference to the distance inside of the material sample or tissue from which backscattered light is being received. In the various embodiment of the present invention, interference between the sample and reference arm light occurs when the paths are made equal to within the coherence length of the source light.

The separation distance (r) from the light injection region on the sample to the one or more backscattered light collection points on the sample may be varied. The separation distance may be modified by changing the position where light is directed into the sample, by changing the position of the light collectors, or by changing both. FIG. 16 shows a compact fiber optic-based device for characterizing the absorption and scattering coefficients of a material. As illustrated, different separation distances (r) between the light injection and collection points can be generated using a fiber optic or optical switch 1612 to address optical fibers or integrated waveguide sample light collectors 1608 at fixed distances from the source injection point. Optionally, the sensor in FIG. 16 may be configured with one or more of the light collectors 1608 functioning as a transceiver; the incident light 1632 may also be directed to the sample through a transceiver.

Detectors that can be used in the present invention may be positioned to measure the intensity of interference between backscattered light from the low coherent light source interacting with the sample coupled with light from the reference arm. The detector generates a signal in that is proportional to the amplitude or intensity of interference between the backscattered light from the sample and light from the reference arm at the optical path length that have been coupled together by a coupler or light combiner. One or more detectors may be used in the present invention. For example, the sensor illustrated in FIG. 14 uses a first detector 1416 and a second light detector 1432. As illustrated in FIG. 14, a second sample light collector 1450 is positioned apart from a first sample light collector 1412. The second sample light collector 1450 is positioned to collect backscattered light from the light source interacting with the sample 1404 with the second detector 1432 generating a second signal. The second signal resulting from interference between the backscattered light collected by 1450 and light 1430 from the reference arm at the optical path length coupled together by a second light combiner 1442. Detectors can consist of a single photodetector, dual-balanced detectors, or an array of photo-detectors followed by appropriate amplification and signal processing. When using a light source or multiple sources capable of operating at several wavelengths simultaneously, in order to distinguish the reflected signal corresponding to each one of the different wavelengths, an array of photodetectors can be used, one photodetector for each wavelength and a grating or similar light dispersion element positioned in front of the array. In general the backscattered light from the sample is collected by a light collector such as an optical fiber, this light is coupled with light from the reference arm at the optical path length and the combined light is applied to a photodetector which converts the intensity of interference to a proportional current-varying electric signal. The current-varying electrical signal from the photodetector may be converted to a voltage-varying signal by a trans-impedance amplifier or other suitable devices.

Various interferometric components may be used in the interferometric sensors of the present invention as well as schemes for noise reduction in low-coherence reflectometry; schemes for improved detection in low-coherence reflectometry; and schemes to measure polarization independent signals. The detectors can be connected with processors and display devices, the output from each detector can be an electrical signal proportional to the intensity of interference measured between the light in the reference arm and light backscattered from the sample at the optical path length. The detector outputs in analog or converted to digital form, optionally conditioned or filtered, are then used to determine the absorption $\mu_a$ and diffusion D (inverse scattering) coefficients of the sample through a function, and preferably a function such as Eq (1) or Eq. (2). The absorption $\mu_a$ and diffusion D coefficients that are determined may then be correlated with the concentration of an analyte in the sample or a type of material present in the sample.

Optical fibers or optical fiber cable which may used in the present invention include single mode optical fibers and polarization maintaining single mode fibers. The use of a single mode fiber is useful in may applications of the sensor because it will propagate and collect a single transverse spatial mode optical light which can be focused to its minimum spot size (the diffraction limit) for a desired application; polarization maintaining fibers may provide for a better signal to noise ratio. Preferably the single mode optical fiber consists of a core, a cladding, and a jacket (not shown). The radiation light is typically guided within the glass core of the fiber which can be 5-9 microns in diameter. The core of the fiber is typically surrounded by a glass cladding (not shown) in order to both facilitate light guiding as well as to add mechanical strength to the fiber. Waveguides and channels used for integrated optical devices are also preferably single mode channels and capable of maintaining light polarization.

The subject invention can also use components commonly utilized in low-coherence interferometers. See U.S. Pat. No. 5,202,745 to Sorin; U.S. Pat. No. 5,323,229 to May; U.S. Pat. No. 5,365,335 to Sorin; U.S. Pat. No. 5,646,724 to Venkatesh; and U.S. Pat. No. 5,847,827 to Fercher, the contents of which are incorporated herein by reference in their entirety.

One embodiment of the present invention may be configured in a housing and used as a laparoscope or an endoscope portions of which are illustrated in FIGS. 25 and 26. An endoscope generally includes a hollow housing forming an elongated bore having a proximal end and a distal end. As shown in FIG. 25 the distal end can include an optical window or port 2516 through which optical radiation is directed toward and collected from the structure 2520 of interest. The housing 2504, which may be stiff or flexible, may include an invasive member such as serrated edge (not shown) at its distal end for cutting tissue to gain access to a cavity. Within the bore of the housing there can reside an first transceiver 2508 and a second transceiver 2512 or a light collector that is separated a distance (r) from the first transceiver. The transceiver and or light collector may be but are not limited to an optical fiber or waveguide. The endoscopic unit both illuminates and collects retroreflected light at the optical path length (s) for the two transceivers.

An irrigation port may be formed near the distal end of the housing (not shown) for irrigating the structure being imaged. A rotational scanning mechanism can be included to rotate transceivers within the housing. The housing may include one or more transparent windows formed on the walls of the distal end of the for transmitting optical radiation to the structure or tissue being analyzed.

Alternatively the sensor of the present invention may be configured as a catheter that includes a guidewire and two transceivers that can be used to illuminate human body channels, such as a tissue mass within a blood vessel, for purposes of diagnosis. The low coherent light source from the transceivers may be used to illuminate the tissue and provides a reference light. Illumination that is backscattered from the tissue is combined with the reference light in an interferometer process. A catheter may be used in the diagnosis and identification of various tissues and growths on the surfaces of such tissues. Various types of placque, growth of blood vessels, and presence of abnormal cells on a tissue may be identified using changes in the diffusion and absorption coefficients of the tissue being probed. The use of the present invention permits characterization of the tissue and can enable the tissue be identified as healthy tissue, abnormal, or diseased tissue.

A catheter may typically include a hollow, thin wall, tubular, stainless steel guidewire that can be directed in a patient and that has a diameter sufficient to remain flexible and to accommodate at least two optical fibers, preferably two transceivers. Without limitation the catheter can be about 2.5 meters in total length, and have about 180 centimeters (cm) in usable length. Throughout the length of catheter two single mode or polarization maintaining optical fibers may be placed to extend within the tube.

At the terminal, or distal end of the catheter can be an optically clear window, or lens, through which low coherent light is delivered to adjacent tissue via the end of optical fibers, and through which reflected light is collected from the tissue for delivery to the fiber end and then to couplers.

As illustrated in FIG. 24, and without wishing to be bound by theory, in a diffusive medium, the pathlength distribution of photons depends on the distance (r) between the points of injection of source light into a sample, points 2440 and 2444 and detection of backscattered light from the sample also points 2440 and 2444. For the specific case photon flux (normal to the interface) the photon distribution is described by Eq. (1).

$$P(r, s) = (4\pi Dc)^{-\frac{3}{2}} z_e s^{-\frac{5}{2}} \exp(-\mu_a s) \exp\left(-\frac{r^2 + z_e^2}{4Ds}\right) \qquad (1)$$

A numerical example is shown in FIG. 4 where P(r,s) is plotted as a function of optical pathlength (s) for increasing values of the separation distance (r) between the points 2440 and 2444 as indicated by the arrow.

Optical parameters which describe the photon distribution in Eq. (1) include D the diffusion coefficient that is inversely proportional to the scattering coefficient,$\mu_a$ the absorption coefficient; $z_e$ the extrapolation length parameter that depends on the boundary conditions, coupling, the path length (s) set by the reference arm of the interferometer, and (r) the distance between the light injection and detection points on the sample.

In the specific case where r is 0, for example a transceiver acting as a source and detector as illustrated by the path 2440 or 2444 in FIG. 24, the pathelength distribution is given by Eq. (2)

$$P(0, s) = (4\pi Dc)^{-\frac{3}{2}} z_e s^{-\frac{5}{2}} \exp(-\mu_a s)\exp\left(-\frac{z_e^2}{4Ds}\right) \quad (2)$$

Figure 8:
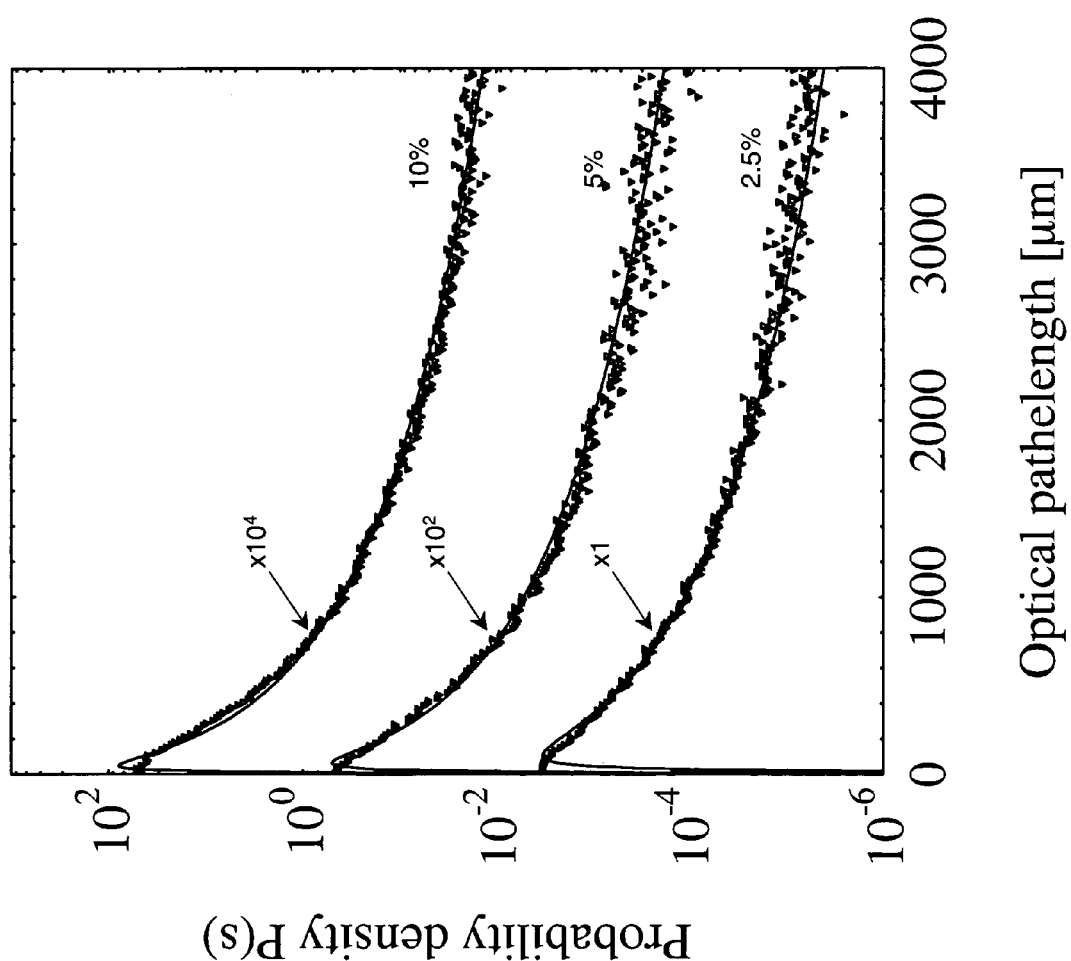
FIG. 8 show experimentally obtained normalized backscattered intensity corresponding to suspensions of polystyrene microspheres with diameters of 0.426 microns with volume fractions of 10%, 5%, and 2.5% (Pospescu et al., Optics Letters, vol. 24, pp.442, (1999) the contents of which are included herein by reference in their entirety). Fit curves were made using an equation similar to Eq (2) vide infra.

The data in FIG. 8 were fit by Eq. (2) which is illustrated by the continuous line.

An advantage of the sensor devices in various embodiments of the present invention is that they allow the determination of D and $\mu_a$ independently. Preferably, by using a plurality of injection and detection points (as illustrated in for example FIG. 15), P(r,s) may be accessed as expressed in Eq. (1). The data can be processed in different ways, for instance: for a fixed (s) or ($s_0$), one can fit P(r,$s_0$) as a function of (r) to obtain D as given in Eq. (3)

$$\ln(P) = \frac{1}{4 \cdot D \cdot s_0} \cdot r^2 + b(s_0) \quad (3)$$

Alternatively, for two different separating distances $r_2$ and $r_1$ as illustrated in FIG. 22, P($r_1$, $s_0$) and P($r_2$, $s_0$) may be determined, and then calculate D as given by Eq. (4):

$$D = \frac{r_1^2 - r_2^2}{4 \cdot s_0 \cdot \ln\left(\frac{P(r_2, s_0)}{P(r_1, s_0)}\right)} \quad (4)$$

As a result of using these equations, D is obtained independent of $\mu_a$. Even more advantageously, D is obtained independent of $z_e$ which accounts for all the coupling and interface effects. This is highly desirable for a sensor that relies on the optical coupling between an optical head and diffuse optically dense material like a polymer composite, human skin, or an organ tissue.

In the practice of the present invention, Eq. (2) may be used to determine the absorption coefficient $\mu_a$. It is important to not that an analyte in a material, for example residual solvent, unreacted monomer, a drug, or a component of blood present in the interstitial fluid can affect both the scattering and absorption coefficients of the material sample. For example, glucose concentration affects both the scattering and absorption coefficients in tissue. By having the scattering and absorption coefficients, a more accurate determination and correlation of various analytes in materials and tissues can be made.

Figure 7:
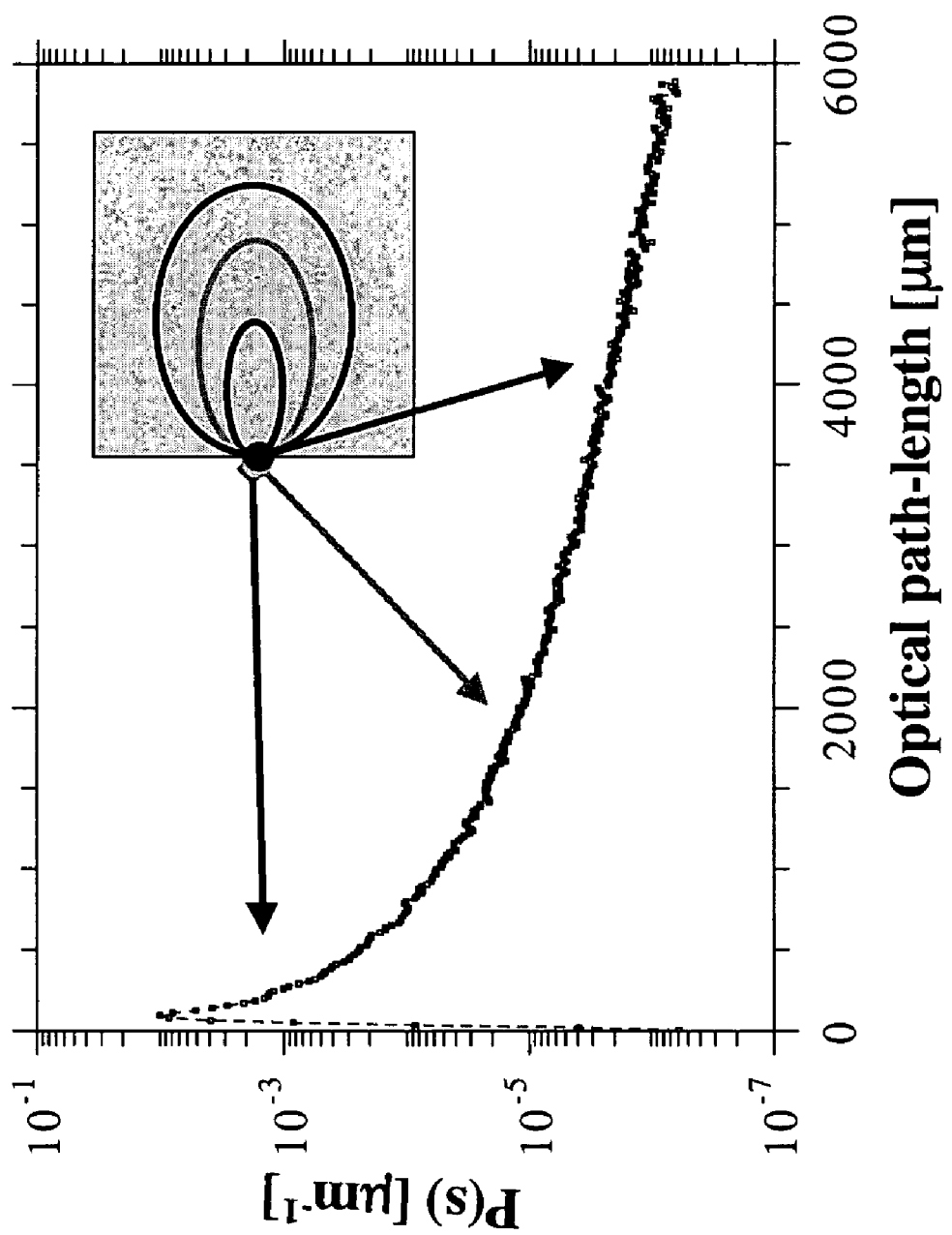
FIG. 7 shows the variation of photon distribution P(s) with optical path length (s).
Figure 9A:
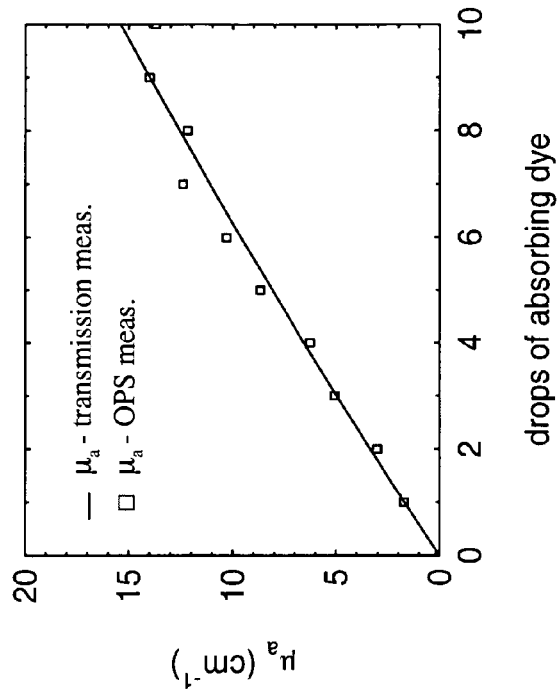
FIG. 9A shows the effect of absorption on the path length distribution.
Figure 9B:
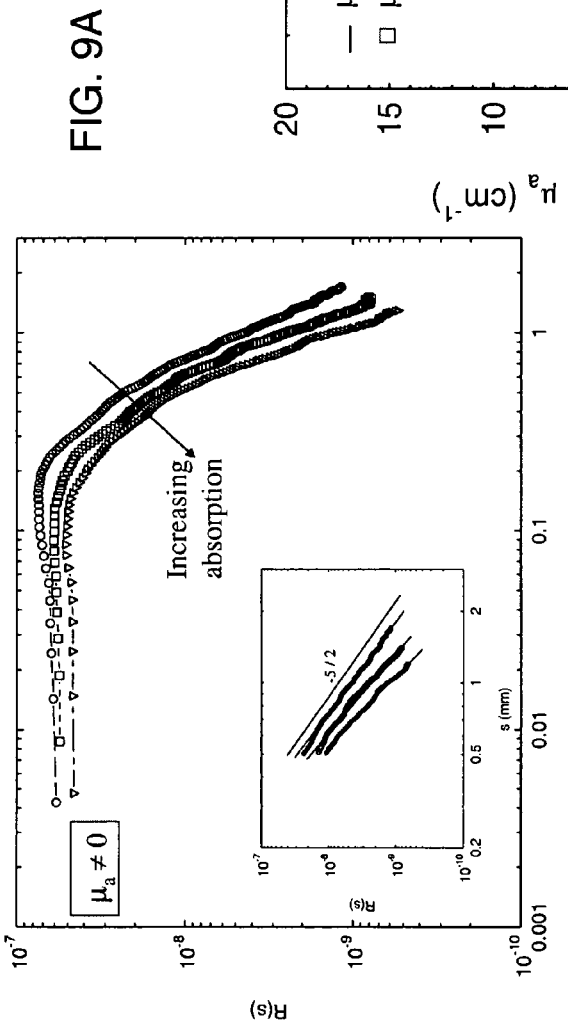
FIG. 9B is an example of how the absorption coefficient can be obtained from processing the pathlength distribution.
Figure 9C:
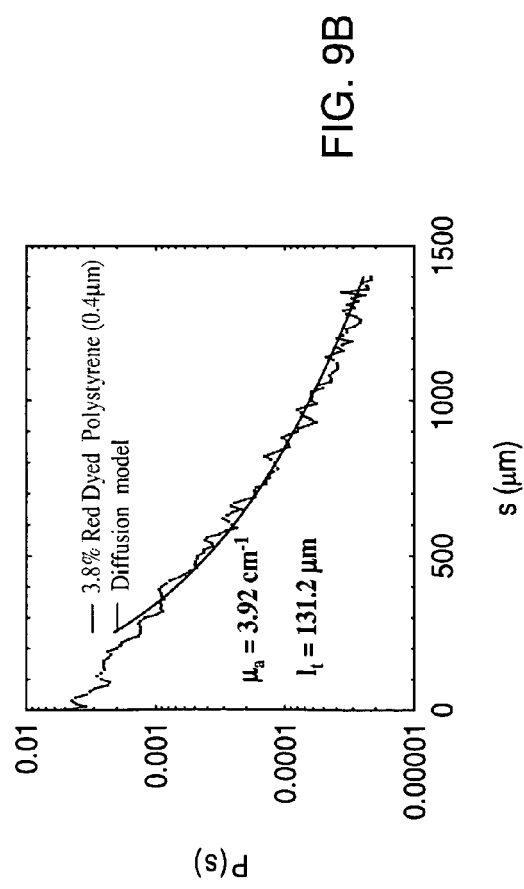
FIG. 9C shows the proportionality between the dye concentration and the absorption coefficient determined by the method shown in 9B.

A typical configuration for measuring the length-resolved reflectance is shown in FIG. 6. A typical distribution of optical path lengths is shown in FIG. 7. As can be seen, the relative contributions of paths with different lengths lead to continuous distribution which is specific to the investigated medium. A typical example is shown in FIG. 8. The distribution depends on both absorption and scattering and can be used to determine changes in absorption that affect differently paths of different lengths. The sensitivity to changes in absorption and the processing procedure are illustrated in FIGS. 9A, 9B and 9C.

An adjustable separation distance (r) between source and detector permits the limiting of interference between absorption and scattering that is needed in order to probe different optical regimes. When two trajectories are selected to have the same length, the separation distance between the ending points at the surface of the medium determine the penetration depth as illustrated in FIG. 10. When the separation distance is small or zero as in FIG. 11A, a long length for the allowed trajectory 1158 is imposed and the light travels a rather tortuous paths in the depth of the sample; the signal for this tortuous path is determined by both scattering and absorption along the trajectory. On the other hand, when the separation distance is increased and the length of the trajectory 1162 is kept the same, the photon path is restricted to develop in the upper layer of the material in an almost straight line as shown in FIG. 11B. Therefore, in the situation depicted in FIG. 11B, a so-called ballistic light propagation regime is obtained where the detected signal is dominated by the absorption properties of the sample. The optical properties of the sample material, and preferably a biological tissue are determined by scattering and absorption coefficients. In the optical sensor of the present invention, one can independently adjust the separation distance (r) between the ending points of the trajectory as schematically illustrated in FIG. 10 and set the optical path length (s). As a result efficient detection of the absorption and diffusion coefficients can be obtained without the effects of coupling and interface effects.

Low coherence interferometry as used in the optical sensor of the present invention is capable of discriminating various materials based on changes in absorption, scattering, and polarization of low coherent light incident on the sample. The optical sensor of the present invention can use fiber-based or integrated optics. The optical sensor of the present invention can use fiber-based or integrated optics. The optical sensor can measure simultaneously, the spectrally resolved scattering and absorption coefficients in a pulsed or synchronized operation.

When referring to the optical properties of human skin, FIG. 5 shows the layered structure of human skin and it is known that the heterogeneous components can vary from individual to individual. Subcutaneous interstitial fluid can be analyzed for total protein, albumin, glucose, glycosaminoglycan or other molecules including drugs and toxins to ascertain the state of a patient. Interstitial fluid may be used as a measure of the concentration of various molecules in a patient or a material sample. In humans, interstitial fluids are present in tissues such as the dermis and epidermis. Molecules such as drugs, metabolites, glucose, and albumin may be monitored using the intersitial fluid of patients. Because of the multiple scattering effect of composite materials, tissue, and skin, optical measurements of either transmission or reflectance will contain tissue scattering information, as well as absorption information. For example, tissue scattering information includes cell size and cell shape, depth of the tissue layer in which scattering occurs, and refractive index of intracellular fluids and extracellular fluid (interstitial fluid). Absorption information includes absorption by tissue components, such as hemoglobin, melanin, and bilirubin, and the overtone absorption of water, glucose, lipids, and other metabolites. In another example, scattering and absorption from a polymer composite having dispersed nanoparticles for fire retardancy is expected to include information about the fire retardant particles, concentration of plasticizer molecules, and concentration of unreacted monomers in the polymer.

Attenuation of incident light is determined by absorption, scattering, and polarization of the light by the material or by a tissue. In the case of a tissue, this attenuation depends upon the state of the tissue and both the scattering and absorption coefficients will have characteristic values for a normal tissue. It is reasonably to expect that the scattering and or absorption coefficients will differ for different types of atherosclerotic plaque and abnormal cell growth, and can be used for tissue identification.

Using the path length resolved backscattering from a tissue like skin, a correlation of the measured diffusion coefficient D and absorption coefficient $\mu_a$ to an analyte concentration such as but not limited to glucose, glycerol or albumin can be made. An apparatus as described in FIGS. 13-20 may be used. Various subjects may be used including those having different skin pigmentation such as but not limited to Asian, Negroid and Caucasian skin.

Tests may be conducted on subjects before a meal or several hours following a meal. Backscattering measurements can be performed on readily accessible portions of the patient's body such as the arm, shoulder, lower leg, or neck. A sensor module having a transceiver and a second detector fiber in contact with a filter substrate that protects the optical fiber but allows contact with the tissue is placed against the tissue. Optionally a temperature measurement of the tissue can be made through the sensor by an embedded RTD. Optionally measurements of the absorption and scattering of tissue sample of a patient obtain from the pathlength distribution of photons may be coupled with a signal from a pulse oximeter, a respiratory monitor, a heart rate monitor or a combination of these. For example, the photon pathlength distribution of photons, and hence absorption and scattering of a tissue may be coupled of periods of arterial pulse by comparing absorption and scattering values obtained during a systolic measurement cycle with similar values obtained during a diastolic measurement cycle.

Backscattered light from the tissue can be made at various optical path lengths which can range upto about 4000 microns. The wavelength of the low coherent source should be capable of penetrating the tissue and may range from about 590 nm to about 1850 nm.

Venous blood samples of the subjects may be taken in the just prior, during or immediately following the backscattering measurement and used for determination of the reference values of glucose, glycerol, or albumin present in the tissue. Standard laboratory tests can be used to determine concentration of these analytes in the blood and in the interstitial tissue. Subcutaneous interstitial fluid for analysis can be obtained from the tissues by the wick method or by aspiration.

Backscattering interference intensity data at different sampling distances, (r), for a light source wavelength can be correlated with the glucose, glycerol, or albumin concentration by a linear least square method to either the diffusion coefficient D or the absorption coefficient $\mu_a$. The backscattering intensity at various path lengths may also be used to derive a correlation to the analyte of interest.

By using different path lengths, the effects of skin color on the measurement and subsequent correlation to analyte concentration may be minimized. Those skilled in the art can use similar analysis and apply this measurement method to other analytes.

The following non-limiting examples are used to illustrate various aspects of the present invention.

EXAMPLE 1

The data shown in FIG. 9 was obtained using a low-coherence interferometer operating at a wavelength of 1300 nm and with a dynamic range of 90 dB. The signal was collected using single mode fibers in close proximity of the medium's interface. The scattering medium consisted of a suspension of polystyrene microspheres in water with a volume fraction of 2% and an average diameter of 0.76 microns. The distance (r) between the single mode fibers, points A and B on the sample, was varied between 60 microns and 2 mm.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. An interferometer based sensor comprising:
   a low coherence light source;
   a light splitter positioned to direct light from said low coherence light source to at least one sample and to at least one reference arm;
   at least one sample light collector for collecting light from the sample disposed apart from a site of light injection into the sample by a separation distance;
   an optical coupler for combining light from the sample and light from the reference arm;
   a detector for detecting interference between the sample light and the light from the reference arm; and
   a processor for determining absorption and scattering of light from the sample based on the interference between the sample light and the light from the reference arm.

2. The sensor of claim 1, further comprising a housing.

3. The sensor of claim 1, wherein the separation distance is less than about 1 centimeter.

4. The sensor of claim 1, comprising at least a first sample light collector and at least one second sample light collector disposed apart from a site of light injection into the sample.

5. The sensor of claim 2, wherein said housing comprises a portion of an endoscope.

6. The sensor of claim 1, wherein the at least one sample light collector samples light having a trajectory dominated by sample absorption.

7. The sensor of claim 1, wherein light is propagated through optical fibers.

8. The sensor of claim 1, wherein the reference light has an optical delay that is fixed, adjustable, or a combination thereof.

9. The sensor of claim 1, further comprising a plurality of light sources, wherein each light source has a different wavelength.

10. The sensor of claim 1, further comprising a plurality of light collectors, each light collector having a different separation distance from the site of light injection into the sample.

11. The sensor of claim 1, further comprising one or more polarizers.

12. A method for characterizing a sample with an interferometer comprising:
propagating low coherence light from a source into a light splitter, said light splitter directing a portion of said low coherence light to one or more sites of light injection on the sample and directing a portion of said low coherence light to a reference arm;
collecting backscattered light from one or more regions of the sample disposed apart from the one or more sites of light injection by a separation distance;
determining the intensity of interference between the low coherence light in said reference arm and the backscattered light from the one or more regions of the sample;
calculating absorption and scattering of the sample from said interference intensities; and
characterizing said sample based on said absorption and scattering.

13. The method of claim 12, wherein the low coherence light is directed onto the sample and backscattered light is collected using one or more transceivers.

14. The method of claim 12, wherein the reference arm is scanned through a plurality of optical path lengths.

15. The method of claim 12, wherein the backscattered light from one or more regions of said sample have different trajectories in the sample.

16. The method of claim 12, further comprising correlating the absorption coefficient and a scattering coefficient to the concentration of an analyte in the sample.

17. The method of claim 12, wherein the sample is heterogeneous.

18. The method of claim 12, further comprising detecting interference between the reference arm light and light backscattered from one or more regions using one or more detectors and measuring the intensity of interference between reference arm light and light backscattered from one or more regions at a distance from the region where said light is directed on said sample.

19. The method of claim 16, wherein said analyte is glucose and said sample is skin.

20. An integrated optical sensor for glucose monitoring in biological tissue, comprising:
means for generating low coherence light;
means for controlling an optical path length of said low coherence light;
means for discriminating between scattering and absorption;
means for recording spectral measurements over a limited range; and
means for determining glucose concentrations based on the spectral measurements.

21. The integrated optical sensor of claim 20, wherein the biological tissue is human skin.

22. The integrated optical sensor of claim 20, wherein the low coherence light source includes a super luminescent diode.

23. The integrated optical sensor of claim 20, wherein the length of the optical path is controlled by an optical delay line.

24. The integrated optical sensor of claim 20, further comprising a plurality of light sources, each light source having a different wavelength.

25. The integrated optical sensor of claim 20, wherein the sensor is designed to limit the interference between light scattering and absorption.

26. The integrated optical sensor of claim 20, wherein the means for generating low coherence light includes an optical fiber based transmission medium.

27. A system for monitoring glucose concentration in biological specimen using the integrated optical sensor of claim 20.

28. The system for monitoring glucose concentration of claim 27, wherein the monitoring is non-invasive.

29. The system for monitoring glucose concentration of claim 27, wherein the monitoring can be synchronized with the heartbeat of the biological specimen.

30. The system for monitoring glucose concentration of claim 27, wherein the biological specimen is a human being.

31. A method for determining glucose concentration using an integrated optical sensor, comprising:
generating low coherence light;
directing said low coherence light into a sample and a reference arm;
controlling a length of the optical path of said low coherence light in said reference arm;
collecting backscattered light from one or more points of said sample disposed apart from a site of light injection into the sample by a separation distance and collecting light from said reference arm;
recording spectral measurements from the backscattered light from one or more points of said sample disposed apart from a site of light injection of low coherence light into the sample by a separation distance and backscattered light from said reference arm over a limited range;
determining the intensity of interference between the backscattered light from reference arm and the backscattered light from the one or more points of said sample disposed apart from a site of light injection of low coherence light into the sample by a separation distance;
calculating an absorption coefficient and a scattering coefficient from the intensity of interference; and
determining glucose concentration based on the absorption coefficient and scattering coefficient.

32. The method of claim 31, wherein the glucose concentration is determined in biological tissue.

33. The method of claim 32, wherein the biological tissue is human skin.

34. The method of claim 31, wherein the low coherence light is generated from a source including a super luminescent diode.

35. The method of claim 31, wherein the length of the optical path is controlled by an optical delay line.

36. An interferometer based sensor comprising:
a low coherence light source;
a reference arm having an optical delay;
a first light splitter positioned to propagate a portion of said source light from said light source to a first site of light injection into said sample and a portion of said light to the reference arm; a first light collector for collecting backscattered light from a first region of said sample at or near the first site of light injection;
a second light splitter positioned to propagate a portion of said source light from said light source to a second site of light injection into said sample and a portion of said light to the reference arm; a second light collector for collecting backscattered light from a second region of said sample disposed apart from the second site of light injection; said second region separated from said first region on said sample;

a first detector that measures the intensity of interference between backscattered light from said first region of said sample and light from said reference arm at the optical delay, said first detector generating a first signal proportional to said interference intensity of said first region;

a second detector that measures the intensity of interference between backscattered light from said second region of said sample and light from said reference arm at the optical delay, said second detector generating a second signal proportional to the interference intensity of said second region; and a processor to determine absorption, scattering, or both of the sample from said first signal and said second signal.

37. The sensor of claim 36, wherein said sensor comprises a portion of an endoscope or a catheter.

38. The sensor of claim 36, wherein the position of said second light collector samples light having a trajectory dominated by sample absorption.

39. The sensor of claim 36, wherein light is propagated through single mode optical fibers, polarization maintaining optical fibers or a combinations thereof.

40. The sensor of claim 36, further comprising one or more polarizer.

41. The sensor of claim 36, wherein the optical delay of the reference arm is adjustable.

42. The sensor of claim 36, wherein the separation distance between the second site of light injection and second region is adjustable.

43. The sensor of claim 36, wherein the separation of the first site of light injection and the first region and second site of light injection and the second region results in two different light trajectories in said sample.

* * * * *